US012773562B2

(12) United States Patent
Ganion et al.

(10) Patent No.: US 12,773,562 B2
(45) **Date of Patent: *Oct. 27, 2026**

(54) MEDICAL DEVICE AND METHOD FOR DETERMINING ATRIOVENTRICULAR SYNCHRONY

(71) Applicant: Medtronic, Inc., Minneapolis, MN (US)

(72) Inventors: Vincent P. Ganion, Blaine, MN (US); Yanina Grinberg, Plymouth, MN (US); Paul R. Solheim, Blaine, MN (US)

(73) Assignee: Medtronic, Inc., Minneapolis, MN (US)

( * ) Notice: Subject to any disclaimer, the term of this patent is extended or adjusted under 35 U.S.C. 154(b) by 205 days.

This patent is subject to a terminal disclaimer.

(21) Appl. No.: 18/508,142

(22) Filed: Nov. 13, 2023

(65) Prior Publication Data

US 2024/0082583 A1 Mar. 14, 2024

Related U.S. Application Data

(63) Continuation of application No. 17/490,292, filed on Sep. 30, 2021, now Pat. No. 11,819,698.

(Continued)

(51) Int. Cl.

*A61N 1/365* (2006.01)
*A61N 1/368* (2006.01)
*A61N 1/37* (2006.01)

(52) U.S. Cl.

CPC ..... *A61N 1/36542* (2013.01); *A61N 1/36521* (2013.01); *A61N 1/36535* (2013.01); *A61N 1/3684* (2013.01); *A61N 1/3706* (2013.01)

(58) Field of Classification Search

CPC ............ A61N 1/36542; A61N 1/36521; A61N 1/36535; A61N 1/3684; A61N 1/3706

See application file for complete search history.

(56) References Cited

U.S. PATENT DOCUMENTS 4,284,082 A * 8/1981 Funke ................. A61N 1/3622 607/9

4,485,813 A 12/1984 Anderson et al.

(Continued)

FOREIGN PATENT DOCUMENTS

WO 2016014352 A1 1/2016
WO 2018165289 A1 9/2018

OTHER PUBLICATIONS (PCT/US2021/054373) PCT Notification of Transmittal of the International Search Report and the Written Opinion of the International Searching Authority, Mailed Jan. 26, 2022, 14 pages.

(Continued)

*Primary Examiner* — William J Levicky

(57) ABSTRACT

A medical device is configured to sense a cardiac signal that includes far field ventricular event signals and determine a ventricular activity metric from the sensed cardiac signal. The ventricular activity metric may be representative of a ventricular rate or an atrioventricular time interval. The medical device is configured to determine an atrioventricular synchrony metric based on the ventricular activity metric and generate an output based on the atrioventricular synchrony metric. The device may include a memory configured to store data corresponding to the atrioventricular synchrony metric.

21 Claims, 11 Drawing Sheets

Related U.S. Application Data

(60) Provisional application No. 63/111,163, filed on Nov. 9, 2020.

(56) References Cited

U.S. PATENT DOCUMENTS

| | | | | |
|---|---|---|---|---|
| 5,052,388 | A | 10/1991 | Sivula et al. | |
| 5,507,782 | A | 4/1996 | Kieval et al. | |
| 5,593,431 | A | 1/1997 | Sheldon | |
| 5,609,613 | A * | 3/1997 | Woodson | A61N 1/36542 607/19 |
| 5,720,769 | A | 2/1998 | van Oort et al. | |
| 5,792,195 | A * | 8/1998 | Carlson | A61N 1/36542 607/18 |
| 5,885,471 | A | 3/1999 | Ruben et al. | |
| 6,044,297 | A | 3/2000 | Sheldon et al. | |
| 7,689,283 | B1 | 3/2010 | Schecter | |
| 7,702,383 | B2 | 4/2010 | Woellenstein et al. | |
| 8,135,463 | B2 | 3/2012 | Burnes et al. | |
| 8,831,705 | B2 | 9/2014 | Dobak | |
| 9,399,140 | B2 | 7/2016 | Cho et al. | |
| 9,724,518 | B2 | 8/2017 | Sheldon et al. | |
| 10,449,366 | B2 | 10/2019 | Splett et al. | |
| 10,532,212 | B2 | 1/2020 | Splett et al. | |
| 10,617,873 | B2 | 4/2020 | Stahmann et al. | |
| 11,819,698 | B2 * | 11/2023 | Ganion | A61B 5/349 |
| 2006/0161211 | A1 | 7/2006 | Thompson et al. | |
| 2008/0021336 | A1 | 1/2008 | Dobak, III | |
| 2009/0198299 | A1 | 8/2009 | Yu et al. | |
| 2014/0121720 | A1 | 5/2014 | Bonner et al. | |
| 2016/0015984 | A1 * | 1/2016 | Demmer | A61N 1/36592 607/18 |
| 2016/0067486 | A1 | 3/2016 | Brown et al. | |
| 2016/0067487 | A1 | 3/2016 | Demmer et al. | |
| 2020/0179707 | A1 | 6/2020 | Splett et al. | |
| 2020/0179708 | A1 | 6/2020 | Splett et al. | |

OTHER PUBLICATIONS

"Office Action Issued in European Patent Application No. 21802507.0-1122", Mailing Date: Oct. 23, 2025, 6 Pages.

* cited by examiner

MEDICAL DEVICE AND METHOD FOR DETERMINING ATRIOVENTRICULAR SYNCHRONY

REFERENCE TO RELATED APPLICATIONS

This application is a Continuation of U.S. patent application Ser. No. 17/490,292 filed Sep. 30, 2021, which claims the benefit of the filing date of provisional U.S. Application Ser. No. 63/111,163, filed Nov. 9, 2020, the entire content of both incorporated herein by reference.

TECHNICAL FIELD

This disclosure relates to a medical device and method for determining atrioventricular (AV) synchrony.

BACKGROUND

During normal sinus rhythm (NSR), the heartbeat is regulated by electrical signals produced by the sino-atrial (SA) node located in the right atrial wall. Each atrial depolarization signal produced by the SA node spreads across the atria, causing the depolarization and contraction of the atria, and arrives at the atrioventricular (AV) node. The AV node responds by propagating a ventricular depolarization signal through the bundle of His of the ventricular septum and thereafter to the bundle branches and the Purkinje muscle fibers of the right and left ventricles, sometimes referred to as the "His-Purkinje system."

Patients with a conduction system abnormality, e.g., SA node dysfunction or poor AV node conduction, bundle branch block, or other conduction abnormalities, may receive a pacemaker to restore a more normal heart rhythm. A single chamber pacemaker coupled to a transvenous lead carrying electrodes positioned in the right atrium may provide atrial pacing to treat a patient having SA node dysfunction. When the AV node is functioning normally, single chamber atrial pacing may sufficiently correct the heart rhythm. The pacing-evoked atrial depolarizations may be conducted normally to the ventricles via the AV node and the His-Purkinje system maintaining normal AV synchrony. Some patients, however, may experience conduction abnormalities of the AV node, e.g., partial or complete AV block. AV block may be intermittent and may evolve over time. In the presence of high-grade AV block, atrial depolarizations are not conducted to the ventricles on every atrial cycle.

A dual chamber pacemaker may be implanted in some patients to sense and pace both the atrial and ventricular chambers to restore and maintain AV synchrony. The dual chamber pacemaker may be coupled to a transvenous atrial lead and a transvenous ventricular lead, for placing electrodes for sensing and pacing in both the atrial and ventricular chambers. The pacemaker itself is generally implanted in a subcutaneous pocket with the transvenous leads tunneled to the subcutaneous pocket. Intracardiac pacemakers have been introduced or proposed for implantation entirely within a patient's heart eliminating the need for transvenous leads. For example, a ventricular intracardiac pacemaker may provide sensing and pacing from within a ventricular chamber of a patient having AV block to provide ventricular rate support. However, without having an atrial lead coupled to the ventricular intracardiac pacemaker, sensing and tracking of atrial events by the ventricular pacemaker to maintain AV synchrony can be a challenge.

SUMMARY

The techniques of this disclosure generally relate to a medical device configured to determine an AV synchrony metric based on atrial and ventricular activity. The techniques may be implemented in an implantable medical device (IMD) that is not delivering ventricular pacing but is capable of sensing at least one cardiac signal for determining an AV synchrony metric based on ventricular activity determined from the cardiac signal. The IMD may be an atrial pacemaker capable of delivering atrial pacing pulses and sensing an atrial signal that includes ventricular event signals in some examples. The AV synchrony metric may indicate the performance of a ventricular pacemaker in maintaining AV synchrony during ventricular pacing. Thus, the techniques disclosed herein may be performed by an IMD for assessing the performance of a ventricular pacemaker in maintaining AV synchrony. The IMD may be configured to make a determination of AV synchrony or AV asynchrony. In some examples, the IMD may be configured to respond to a determination of AV asynchrony by adjusting an atrial pacing parameter and/or transmitting a signal indicating the AV asynchrony.

In one example, the disclosure provides a medical device including a sensing circuit configured to sense a cardiac signal that includes far field ventricular event signals and a control circuit configured to determine a ventricular activity metric from the sensed cardiac signal. The ventricular activity metric may be representative of at least one of a ventricular rate and/or an atrioventricular time interval. The control circuit is configured to determine an atrioventricular synchrony metric based on the ventricular activity metric and generate an output based on the atrioventricular synchrony metric. The medical device may include a memory configured to store data corresponding to the atrioventricular synchrony metric in response to the output generated by the control circuit.

In another example, the disclosure provides a method including sensing a cardiac signal that includes far field ventricular event signals and determining a ventricular activity metric from the sensed cardiac signal. The ventricular activity metric may be representative of at least one of a ventricular rate and/or an atrioventricular time interval. The method includes determining an atrioventricular synchrony metric based on the ventricular activity metric and generating an output based on the atrioventricular synchrony metric. The method may include storing data corresponding to the atrioventricular synchrony metric in a memory in response to the output.

In another example, the disclosure provides a non-transitory, computer-readable storage medium comprising a set of instructions which, when executed by a control circuit of a medical device, cause the medical device to sense a cardiac signal that includes far field ventricular event signals and determine a ventricular activity metric from the sensed cardiac signal. The ventricular activity metric may be representative of at least one of a ventricular rate and/or an atrioventricular time interval. The instructions further cause the medical device to determine an atrioventricular synchrony metric based on the ventricular activity metric and generate an output based on the atrioventricular synchrony metric. The instructions may cause the medical device to store data corresponding to the atrioventricular synchrony metric in a memory in response to the output.

Further disclosed herein is the subject matter of the following clauses:

1. A medical device comprising:
   - a sensing circuit configured to sense a cardiac signal that includes far field ventricular event signals;

a control circuit configured to:

determine a ventricular activity metric from the sensed cardiac signal, the ventricular activity metric representative of at least one of a ventricular rate and an atrioventricular time interval;

determine an atrioventricular synchrony metric based on the ventricular activity metric; and generate an output based on the atrioventricular synchrony metric; and a memory configured to store data corresponding to the atrioventricular synchrony metric in response to the output generated by the control circuit.

2. The medical device of clause 1, wherein the control circuit is configured to: determine the ventricular activity metric by determining a count of atrial cycles comprising a far field ventricular event signal present in the cardiac signal.

3. The medical device of clause 2, wherein the control circuit is configured to: generate the output by generating a histogram of atrial cycle counts comprising a far field ventricular event signal present in the atrial signal and atrial cycle counts without a far field ventricular event signal present in the cardiac signal.

4. The medical device of any of clauses 1-3, wherein the control circuit is configured to:

determine the ventricular activity metric by determining an integration metric of the cardiac signal over an integration time interval.

5. The medical device of clause 4, wherein the control circuit is configured to:

determine the atrioventricular synchrony metric by normalizing the integration metric by a number of atrial cycles that occur during the integration time interval.

6. The medical device of any of clauses 1-5, wherein the control circuit is configured to:

determine the ventricular activity metric by determining a plurality of atrioventricular time intervals from the cardiac signal, each atrioventricular time interval being the time interval from an atrial event to a far field ventricular event signal; and determine the atrioventricular synchrony metric based on the atrioventricular time intervals.

7. The medical device of any of clauses 1-6, wherein the sensing circuit is configured to sense the cardiac signal by sensing an accelerometer signal 8. The medical device of any of clauses 1-6, wherein the sensing circuit is configured to sense the cardiac signal by sensing an atrial electrical signal.

9. The medical device of any of clauses 1-8, comprising a telemetry circuit configured to transmit data corresponding to the atrioventricular synchrony metric stored in the memory.

10. The medical device of clause 9, wherein:

the control circuit is configured to determine atrioventricular asynchrony based on the atrioventricular synchrony metric; and the telemetry circuit is configured to transmit a signal indicating atrioventricular asynchrony is determined.

11. The medical device of any of clauses 1-10, comprising a pulse generator configured to deliver atrial pacing pulses according to an atrial pacing parameter, wherein:

the control circuit is configured to determine atrioventricular asynchrony based on the atrioventricular synchrony metric; and adjust the atrial pacing parameter in response to determining the atrioventricular asynchrony.

12. The medical device of clause 11, wherein the control circuit is configured to:

decrease an atrial pacing rate in response to determining the atrioventricular asynchrony;

determine an increase in ventricular activity during the decreased atrial pacing rate based on the sensed cardiac signal;

determine cross-chamber oversensing by a ventricular pacemaker in response to determining the increase in ventricular activity; and adjust the atrial pacing parameter in response to determining the cross-chamber oversensing.

13. The medical device of any of clauses 11-12, wherein the control circuit adjusts the atrial pacing parameter by disabling atrial pacing by the pulse generator.

14. The medical device of clause 13, wherein the control circuit is further configured to:

determine an atrioventricular synchrony monitoring condition is met; and re-enable the atrial pacing by the pulse generator in response to the atrioventricular synchrony monitoring condition being met.

15. The medical device of clause 14, further comprising an accelerometer producing an accelerometer signal, wherein the control circuit is configured to determine the atrioventricular synchrony monitoring condition is met by determining at least one of:

an expired time interval;

a change in pacing impedance;

a change in a patient posture determined from the accelerometer signal;

a change in a patient physical activity level determined from the accelerometer signal;

a change in an atrial rate; or a change in a ventricular rate.

16. A method, comprising:

sensing a cardiac signal that includes far field ventricular event signals;

determining a ventricular activity metric from the sensed cardiac signal, the ventricular activity metric representative of at least one of a ventricular rate and an atrioventricular time interval;

determining an atrioventricular synchrony metric based on the ventricular activity metric;

generating an output based on the atrioventricular synchrony metric; and storing data in a memory in response to the output, the data corresponding to the atrioventricular synchrony metric.

17. The method of clause 16, wherein determining the ventricular activity metric comprises determining a count of atrial cycles comprising a far field ventricular event signal present in the cardiac signal.

18. The method of clause 17, wherein generating the output comprises generating a histogram of atrial cycle counts comprising a far field ventricular event signal present in the cardiac signal and atrial cycle counts without a far field ventricular event signal present in the cardiac signal.

19. The method of any of clauses 16-18, wherein determining the ventricular activity metric comprises determining an integration metric of the cardiac signal over an integration time interval.

20. The method of clause 19, wherein determining the atrioventricular synchrony metric comprises normalizing the integration metric by a number of atrial cycles that occur during the integration time interval.

21. The method of any of clauses 16-20, wherein:
 determining the ventricular activity metric comprises determining a plurality of atrioventricular time intervals from the cardiac signal, each atrioventricular time interval being the time interval from an atrial event to a far field ventricular event signal in the cardiac signal; and
 determining the atrioventricular synchrony metric based on the atrioventricular time intervals.
22. The method of any of clauses 16-21, wherein sensing the cardiac signal comprises sensing an accelerometer signal.
23. The method of any of clauses 16-21, wherein the sensing the cardiac signal comprises sensing an atrial electrical signal.
24. The method of any of clauses 16-23, further comprising transmitting the stored data corresponding to the atrioventricular synchrony metric.
25. The method of any of clauses 16-24, comprising:
 determining atrioventricular asynchrony based on the atrioventricular synchrony metric; and
 transmitting a signal indicating atrioventricular asynchrony is determined.
26. The method of any of clauses 16-25, comprising:
 determining atrioventricular asynchrony based on the atrioventricular synchrony metric; and
 adjusting an atrial pacing parameter in response to determining the atrioventricular asynchrony.
27. The method of clause 26, comprising:
 decreasing an atrial pacing rate in response to determining the atrioventricular asynchrony;
 determining an increase in ventricular activity during the decreased atrial pacing rate based on the sensed cardiac signal;
 determining cross-chamber oversensing by a ventricular pacemaker in response to determining the increase in ventricular activity; and
 adjusting an atrial pacing parameter in response to determining the cross-chamber oversensing.
28. The method of any of clauses 26-27, comprising adjusting the atrial pacing parameter by disabling atrial pacing.
29. The method of clause 28, comprising:
 determining an atrioventricular synchrony monitoring condition is met; and
 re-enabling the atrial pacing in response to the atrioventricular synchrony monitoring condition being met.
30. The method of clause 29, wherein determining the atrioventricular synchrony monitoring condition is met by at least one of:
 determining a time interval is expired since disabling atrial pacing;
 determining a change in pacing impedance;
 sensing an accelerometer signal and determining a change in a patient posture from the accelerometer signal;
 sensing an accelerometer signal and determining a change in a patient physical activity level from the accelerometer signal;
 a change in an atrial rate; or
 a change in a ventricular event rate.
31. A non-transitory, computer-readable storage medium comprising a set of instructions which, when executed by a control circuit of a medical device, cause the medical device to:
 sense a cardiac signal that includes far field ventricular event signals;
 determine a ventricular activity metric from the sensed cardiac signal, the ventricular activity metric representative of at least one of a ventricular rate and an atrioventricular time interval;
 determine an atrioventricular synchrony metric based on the ventricular activity metric;
 generate an output based on the atrioventricular synchrony metric; and
 store data in a memory in response to the output, the data corresponding to the atrioventricular synchrony metric.
32. A medical device comprising:
 a sensing circuit configured to sense a cardiac signal that includes far field ventricular event signals;
 a control circuit configured to:
  determine a ventricular activity metric from the sensed cardiac signal, the ventricular activity metric representative of at least one of a ventricular rate and an atrioventricular time interval;
  determine an atrioventricular synchrony metric based on the ventricular activity metric; and
  generate an output based on the atrioventricular synchrony metric; and
 a memory configured to store data corresponding to the atrioventricular synchrony metric in response to the output generated by the control circuit.
33. The medical device of clause 32, wherein the control circuit is configured to:
 determine the ventricular activity metric by determining a count of atrial cycles comprising a far field ventricular event signal present in the cardiac signal.
34. The medical device of any of clauses 32-33, wherein the control circuit is configured to:
 determine the ventricular activity metric by determining an integration metric of the cardiac signal over an integration time interval.
35. The medical device of clause 34, wherein the control circuit is configured to: determine the atrioventricular synchrony metric by normalizing the integration metric by a number of atrial cycles that occur during the integration time interval.
36. The medical device of any of clauses 32-35, wherein the control circuit is configured to:
 determine the ventricular activity metric by determining a plurality of atrioventricular time intervals from the cardiac signal, each atrioventricular time interval being a time interval from an atrial event to a far field ventricular event signal; and
 determine the atrioventricular synchrony metric based on the atrioventricular time intervals.
37. The medical device of any of clauses 32-36, wherein the sensing circuit comprises at least one of an accelerometer configured to sense the cardiac signal by sensing an accelerometer signal and a cardiac electrical signal sensing circuit configured to sense the cardiac signal by sensing an atrial electrical signal.
38. The medical device of any of clauses 32-37, further comprising a telemetry circuit configured to transmit data corresponding to the atrioventricular synchrony metric stored in the memory.
39. The medical device of any of clauses 32-37, further comprising:
 a telemetry circuit configured to transmit data corresponding to the atrioventricular synchrony metric stored in the memory; and
 a pulse generator configured to deliver atrial pacing pulses according to an atrial pacing parameter;
 wherein the control circuit is further configured to:
  determine atrioventricular asynchrony based on the atrioventricular synchrony metric; and in response to determining the atrioventricular asynchrony, at least one of:

control the telemetry circuit to transmit a signal indicating atrioventricular asynchrony is determined; and adjust an atrial pacing parameter used by the pulse generator to deliver atrial pacing pulses in response to determining the atrioventricular asynchrony.

40. The medical device of any of clauses 32-39, further comprising a pulse generator configured to deliver atrial pacing pulses;

wherein the control circuit is further configured to:

determine atrioventricular asynchrony based on the atrioventricular synchrony metric;

decrease an atrial pacing rate in response to determining the atrioventricular asynchrony;

determine an increase in ventricular activity during the decreased atrial pacing rate based on the sensed cardiac signal;

determine cross-chamber oversensing by a ventricular pacemaker in response to determining the increase in ventricular activity; and adjust the atrial pacing parameter in response to determining the cross-chamber oversensing.

41. The medical device of any of clauses 32-40, further comprising a pulse generator configured to deliver atrial pacing pulses;

wherein the control circuit is further configured to:

determine atrioventricular asynchrony based on the atrioventricular synchrony metric; and disable atrial pacing pulse delivery by the pulse generator in response to determining atrioventricular asynchrony.

42. The medical device of clause 41, wherein the control circuit is further configured to:

determine an atrioventricular synchrony monitoring condition is met; and re-enable the atrial pulse delivery by the pulse generator in response to the atrioventricular synchrony monitoring condition being met.

43. The medical device of clause 42, further comprising an accelerometer producing an accelerometer signal, wherein the control circuit is configured to determine the atrioventricular synchrony monitoring condition is met by determining at least one of:

an expiration of a time interval since disabling the delivery of atrial pacing pulses;

a change in pacing impedance;

a change in a patient posture determined from the accelerometer signal;

a change in a patient physical activity level determined from the accelerometer signal;

a change in an atrial rate; or a change in a ventricular rate.

44. A method, comprising:

sensing a cardiac signal that includes far field ventricular event signals;

determining a ventricular activity metric from the sensed cardiac signal, the ventricular activity metric representative of at least one of a ventricular rate and an atrioventricular time interval;

determining an atrioventricular synchrony metric based on the ventricular activity metric;

generating an output based on the atrioventricular synchrony metric; and storing data in a memory in response to the output, the data corresponding to the atrioventricular synchrony metric.

45. The method of clause 44, wherein determining the ventricular activity metric comprises determining a count of atrial cycles comprising a far field ventricular event signal present in the cardiac signal.

46. The method of any of clauses 44-45, wherein determining the ventricular activity metric comprises determining an integration metric of the cardiac signal over an integration time interval.

47. The method of clause 46, wherein determining the atrioventricular synchrony metric comprises normalizing the integration metric by a number of atrial cycles that occur during the integration time interval.

48. The method of any of clauses 44-47, wherein:

determining the ventricular activity metric comprises determining a plurality of atrioventricular time intervals from the cardiac signal, each atrioventricular time interval being a time interval from an atrial event to a far field ventricular event signal in the cardiac signal; and determining the atrioventricular synchrony metric based on the atrioventricular time intervals.

49. The method of any of clauses 44-48, wherein sensing the cardiac signal comprises at least one of sensing an accelerometer signal and sensing an atrial electrical signal.

50. The method of any of clauses 44-49, further comprising transmitting the stored data corresponding to the atrioventricular synchrony metric.

51. The method of any of clauses 44-49, further comprising:

determining atrioventricular asynchrony based on the atrioventricular synchrony metric; and in response to determining the atrioventricular asynchrony at least one of:

transmitting a signal indicating atrioventricular asynchrony is determined; and adjusting an atrial pacing parameter used for generating atrial pacing pulses.

52. The method of any of clauses 44-51, comprising:

determining atrioventricular asynchrony based on the atrioventricular synchrony metric;

decreasing an atrial pacing rate in response to determining the atrioventricular asynchrony;

determining an increase in ventricular activity during the decreased atrial pacing rate based on the sensed cardiac signal;

determining cross-chamber oversensing by a ventricular pacemaker in response to determining the increase in ventricular activity; and adjusting an atrial pacing parameter in response to determining the cross-chamber oversensing.

53. The method of any of clauses 44-52, further comprising:

determining atrioventricular asynchrony based on the atrioventricular synchrony metric; and disabling atrial pacing in response to determining the atrioventricular asynchrony.

54. The method of clause 53, further comprising:

determining an atrioventricular synchrony monitoring condition is met; and re-enabling the atrial pacing in response to the atrioventricular synchrony monitoring condition being met.

55. The method of clause 54, wherein determining the atrioventricular synchrony monitoring condition is met by at least one of:
- determining a time interval is expired since disabling the atrial pacing;
- determining a change in pacing impedance;
- sensing an accelerometer signal and determining a change in a patient posture from the accelerometer signal;
- sensing an accelerometer signal and determining a change in a patient physical activity level from the accelerometer signal;
- determining a change in an atrial rate; or
- determining a change in a ventricular rate.

56. A non-transitory, computer-readable storage medium comprising a set of instructions which, when executed by a control circuit of a medical device, cause the medical device to:
- sense a cardiac signal that includes far field ventricular event signals;
- determine a ventricular activity metric from the sensed cardiac signal, the ventricular activity metric representative of at least one of a ventricular rate and an atrioventricular time interval;
- determine an atrioventricular synchrony metric based on the ventricular activity metric;
- generate an output based on the atrioventricular synchrony metric; and
- store data in a memory in response to the output, the data corresponding to the atrioventricular synchrony metric.

The details of one or more aspects of the disclosure are set forth in the accompanying drawings and the description below. Other features, objects, and advantages of the techniques described in this disclosure will be apparent from the description and drawings, and from the claims.

DETAILED DESCRIPTION

Figure 1:
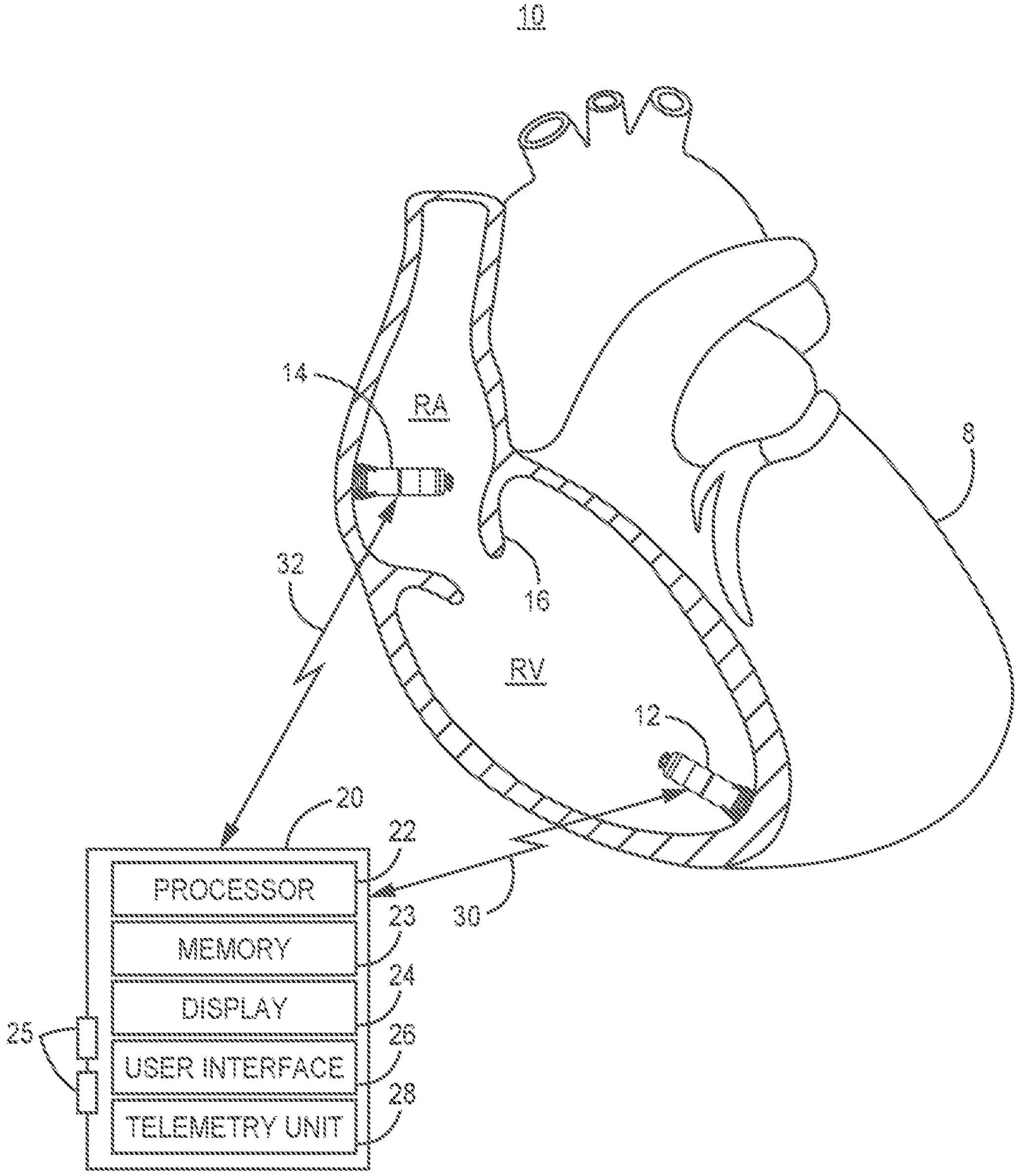
FIG. 1 is a conceptual diagram illustrating an implantable medical device (IMD) system that may be used to sense cardiac electrical signals and cardiac mechanical signals induced by cardiac motion and flowing blood and provide pacing therapy to a patient's heart.

In general, this disclosure describes techniques that may be performed by a medical device for determining the performance of a ventricular pacemaker in maintaining AV synchrony. A processor of a medical device may receive a cardiac signal, which may be an atrial signal sensed from an atrial heart chamber, and determine a metric of ventricular activity from the sensed cardiac signal. An "atrial signal" as used herein, refers to a signal that is sensed using a sensor that is located outside and away from a ventricular chamber, such as in or on an atrial chamber. The term "ventricular activity" refers to the rate and/or relative timing of ventricular electrical depolarizations or ventricular beats. The ventricular activity metric may be determined based on far field ventricular event signals, which may be electrical event signals, e.g., FFRWs, corresponding to ventricular myocardial depolarizations when the received cardiac signal is a cardiac electrical signal sensed from a non-ventricular location. The ventricular activity metric may be determined based on ventricular event signals that are far field mechanical event signals, e.g. corresponding to ventricular contraction and/or relaxation, e.g., when the sensed atrial signal is an acceleration signal, pressure signal or other type of mechanical signal. As used herein the term "far field" refers to a signal that is sensed remotely from the origin of the signal. As such, a "far field ventricular signal" is a signal arising from ventricular electrical or mechanical activity that is sensed remotely or away from the ventricular chambers of the heart, e.g., from an atrial location, from a subcutaneous or submuscular location, from a venous location, from a cutaneous location or any other location other than from within or on a ventricular chamber.

The ventricular activity metric may be correlated to or representative of the ventricular rate and/or the relative timing of far field ventricular event signals to atrial events in some examples. For instance, the ventricular activity metric may be a count of far field ventricular events sensed from an atrial signal, an integration of the atrial signal that includes far field ventricular event signals, or another metric correlated to the rate of ventricular events. In other examples, the ventricular activity metric may be determined as an AV interval from an atrial event to the next far field ventricular event signal sensed from the atrial signal.

Based on the ventricular activity metric, the processor of the medical device may determine an AV synchrony metric that indicates how well-synchronized ventricular events are with atrial events. The AV synchrony metric is therefore representative of the performance of a ventricular pacemaker in maintaining AV synchrony. For example, the AV synchrony metric may be a count or percentage of atrial cycles that include a ventricular event, which may be required to be within an expected AV interval of an atrial event, sensed or paced. In another example, the AV synchrony metric is an integration metric of the ventricular event signals in the atrial signal determined as the ventricular activity metric and normalized by the rate or number of atrial events during an integration time interval to determine the AV synchrony metric. In yet another example, the AV synchrony metric is a measure of centeredness or spread of AV intervals determined as time intervals from an atrial event to the immediately following far field ventricular event signal.

The cardiac signal may be sensed by electrodes or another sensor, such as an accelerometer, in or on the atrium such that the ventricular event signals are far field event signals included in an atrial signal. The far field ventricular event signals may correspond to intrinsic ventricular events and/or paced ventricular events when ventricular pacing is being delivered by a different medical device, e.g., an intracardiac ventricular pacemaker. The AV synchrony metric is therefore based on far field ventricular event signals in a cardiac signal sensed by a device that is not delivering the ventricular pacing. In this way, a first device senses a signal that includes far field ventricular event signals analyzed to determine an AV synchrony metric that is an assessment of the performance of a second device that is configured to deliver atrial synchronized ventricular pacing.

In the illustrative examples presented herein, the techniques for determining a ventricular activity metric and an AV synchrony metric for assessing the performance of a ventricular pacemaker in maintaining AV synchrony are described as being performed by an atrial pacemaker. It is contemplated, however, that the techniques may be performed by a medical device having electrodes and/or other sensor(s) for sensing cardiac signals remotely from the ventricles such that the cardiac signals include atrial event signals attendant to atrial intrinsic or paced depolarizations or contractions and far field ventricular event signals attendant to ventricular intrinsic or paced depolarizations or contractions. Other medical devices that may be configured to perform techniques disclosed herein for determining an AV synchrony metric and generating an output in response to the AV synchrony metric may include, but are not limited to, a subcutaneous implantable cardioverter defibrillator (ICD), which may be coupled to a suprasternal or substernal lead for sensing cardiac electrical signals, or an implantable cardiac monitor such as the REVEAL LINQ® Insertable Cardiac Monitor, available from Medtronic, Inc., Minneapolis, MN. Accordingly, the techniques disclosed herein attributed to an atrial pacemaker as described below in conjunction with FIG. 1 and other drawings presented herein are not limited to practice with an atrial pacemaker but may be implemented in a variety of implantable or wearable medical devices capable of sensing cardiac signals remotely from a ventricular chamber but including far field ventricular event signals for assessing the AV synchrony performance of another device that is implanted in the patient for delivering atrial synchronized ventricular pacing.

FIG. 1 is a conceptual diagram illustrating an IMD system 10 that may be used to sense cardiac signals and provide pacing therapy to a patient's heart 8. IMD system 10 is shown including an atrial pacemaker 14 implanted within the right atrium (RA). Pacemaker 14 may be a transcatheter leadless pacemaker which is implantable wholly within a heart chamber, e.g., wholly within the right atrium (RA) of heart 8 for sensing atrial signals and delivering atrial pacing pulses from within the atrium. Atrial pacemaker 14 is shown positioned in the RA, e.g., along the lateral endocardial wall though other endocardial or epicardial locations are possible, within or on an atrial chamber in different locations than the location shown.

IMD system 10 includes ventricular pacemaker 12 implanted in the right ventricle (RV). Ventricular pacemaker 12 may also be a transcatheter leadless pacemaker, which may be wholly implantable within a ventricular heart chamber for sensing cardiac signals and delivering ventricular pacing pulses. Pacemakers 12 and 14 may be reduced in size compared to subcutaneously implanted pacemakers and may be generally cylindrical in shape to enable transvenous implantation via a delivery catheter.

Pacemakers 12 and 14 may include housing-based electrodes for sensing cardiac electrical signals and delivering pacing pulses. Atrial pacemaker 14 includes cardiac electrical signal sensing circuitry configured to sense atrial P-waves attendant to the depolarization of the atrial myocardium and a pulse generator for generating and delivering atrial pacing pulses in the absence of sensed atrial P-waves. Atrial pacemaker 14 may be configured to deliver atrial pacing therapy for treating a sinus node dysfunction, for example. The cardiac electrical signal sensing circuitry of atrial pacemaker 14 may be configured to sense far-field R-waves (FFRWs) from the atrial electrical signal sensed from within the RA using the housing-based electrodes. The FFRWs arise from the depolarization of the ventricular myocardium, due to intrinsic ventricular depolarizations and/or pacing evoked ventricular depolarizations. In some examples, P-wave sensing and FFRW sensing is performed by atrial pacemaker 14 for use in determining the performance of ventricular pacemaker 12 in maintaining AV synchrony.

Ventricular pacemaker 12, also referred to herein as "RV pacemaker 12," includes cardiac electrical signal sensing circuitry configured to sense ventricular R-waves and, in some examples, far-field P-waves from within the RV using the housing-based electrodes. RV pacemaker 12 may deliver ventricular pacing pulses at an AV pacing interval from a sensed far-field P-wave. In other examples, RV pacemaker 12 includes an accelerometer that generates an intraventricular acceleration signal. RV pacemaker 12 may deliver ventricular pacing pulses at an AV pacing interval from an atrial acceleration signal sensed from an accelerometer signal sensed from within the RV. It is contemplated that an atrial event signal may be sensed from a cardiac electrical or mechanical signal sensed from within the RV for controlling ventricular pacing pulses in order to promote AV synchrony by RV pacemaker 12. When an atrial event is not sensed by RV pacemaker 12, or when the atrial rate is greater than an atrial tracking rate limit, RV pacemaker 12 may deliver ventricular pacing in a non-atrial tracking pacing mode to provide ventricular rate support, which may be asynchronous to atrial activity, e.g., asynchronous to atrial P-waves or atrial pacing pulses.

Atrial pacemaker 14 may be configured to sense an atrial mechanical signal. The mechanical signal may be a motion signal sensed by a motion sensor, e.g., an accelerometer, enclosed within or on the housing of the atrial pacemaker 14. Atrial mechanical event signals, e.g., corresponding to atrial contraction and/or relaxation, and far field ventricular mechanical event signals, e.g., corresponding to ventricular contraction and/or relaxation, and/or the associated opening/closure of the heart valves, may be present in an accelerometer signal produced by an accelerometer located within or on the atrial chamber, e.g., included in atrial pacemaker 14. Far-field ventricular mechanical event signals may be present in an intra-atrial accelerometer signal sensed by atrial pacemaker 14 in addition to atrial mechanical event signals corresponding to atrial contraction. For example, acceleration of blood due to closure of the tricuspid valve 16 between the RA and RV, the mitral valve between the left atrium and the left ventricle, opening and closure of the semilunar valves (aortic and pulmonic) and the heart motion due to ventricular contraction and relaxation may produce far field ventricular event signals in an intra-atrial cardiac accelerometer signal.

According to techniques disclosed herein, atrial pacemaker 14 may sense far field ventricular events from the accelerometer signal for determining an AV synchrony metric representative of the performance of ventricular pacemaker 12 in delivering atrial synchronized ventricular pacing pulses. Ventricular pacemaker 12 may sense atrial events, either electrical far-field P-waves and/or or mechanical atrial events from an intraventricular accelerometer signal, and set an AV interval for controlling delivery of ventricular pacing pulses in synchrony with sensed atrial events. In other examples, RV pacemaker 12 and/or atrial pacemaker 14 may include other types of sensors for sensing a cardiac signal such as a pressure sensor, a flow sensor, or other sensor capable of generating a signal that includes event signals corresponding to the mechanical contraction and/or relaxation of the ventricles and/or atria and/or valve opening and closing. As described below, atrial pacemaker 14 includes a control circuit with processing circuitry that is configured to detect far field ventricular event signals from one or both of the atrial electrical signal and the atrial acceleration signal for determining the performance of ventricular pacemaker 12 in maintaining AV synchrony, without requiring communication signals transmitted between ventricular pacemaker 12 and atrial pacemaker 14.

Pacemakers 12 and 14 may each be capable of bidirectional wireless communication with an external device 20 for programming various control parameters, including sensing and pacing control parameters, which may be utilized for sensing cardiac events and delivering pacing pulses. External device 20 is often referred to as a "programmer" because it is typically used by a physician, technician, nurse, clinician or other qualified user for programming operating parameters in pacemaker 12 or 14. External device 20 may be located in a clinic, hospital or other medical facility. External device 20 may alternatively be embodied as a home monitor or a handheld device which may be a tablet, cell phone or other personal device that may be used in a medical facility, in the patient's home, or another location. Aspects of external device 20 may generally correspond to the external programming/monitoring unit disclosed in U.S. Pat. No. 5,507,782 (Kieval, et al.), hereby incorporated herein by reference in its entirety. An example programmer that may be configured to perform the techniques disclosed herein is the CARELINK® Programmer, commercially available from Medtronic, Inc., Minneapolis, Minnesota, USA.

External device 20 may include a processor 22, memory 23, display unit 24, user interface 26 and telemetry unit 28. Processor 22 controls external device operations and processes data and signals received from pacemakers 12 and 14. Processor 22 executes instructions stored in memory 23. Processor 22 may include any one or more of a microprocessor, a controller, a digital signal processor (DSP), an application specific integrated circuit (ASIC), a field-programmable gate array (FPGA), or equivalent discrete or analog logic circuitry. In some examples, processor 22 may include multiple components, such as any combination of one or more microprocessors, one or more controllers, one or more DSPs, one or more ASICs, or one or more FPGAs, as well as other discrete or integrated logic circuitry. The functions attributed to processor 22 herein may be embodied as software, firmware, hardware or any combination thereof.

Display unit 24, which may include a graphical user interface (GUI), displays data and other information to a user for reviewing pacemaker operation and programmed parameters as well as cardiac electrical signals retrieved from ventricular pacemaker 12 or atrial pacemaker 14. Processor 22 may receive sensed cardiac signals from atrial pacemaker 14 for processing and analysis according to the techniques disclosed herein. External device processor 22 may be configured to receive atrial signals and/or AV synchrony-related data derived therefrom from atrial pacemaker 14 and generate an output representative of AV synchrony related data, which may be a GUI displayed by display unit 24. The GUI may enable a user to view a representation of AV synchrony related data and in some examples interact with the GUI for selecting different views or representations of the data, request data from atrial pacemaker 14, and/or transmit programming commands. A user interacting with the GUI may adjust programmable parameters by generating programming commands that are transmitted to RV pacemaker 12 and/or atrial pacemaker 14. Programmable parameters may include cardiac signal sensing and cardiac pacing control parameters used by the respective pacemaker 12 or 14.

Memory 23 may include any volatile, non-volatile, magnetic, optical, or electrical media, such as a random access memory (RAM), read-only memory (ROM), non-volatile RAM (NVRAM), electrically-erasable programmable ROM (EEPROM), flash memory, or any other digital or analog media. Memory 23 may be configured to store programmable settings of sensing control parameters used for sensing atrial and ventricular events and pacing therapy delivery control parameters. Memory 23 may store AV synchrony related data received or determined by processor 22 for use in generating an output representative of the determined AV synchrony as disclosed herein.

User interface 26 may include a mouse, touch screen, key pad or the like to enable a user to interact with external device 20 to initiate a telemetry session with RV pacemaker 12 or atrial pacemaker 14 for retrieving data from and/or transmitting data to pacemaker RV 12 or atrial pacemaker 14, including programmable parameters for controlling cardiac event sensing and therapy delivery. A clinician may use user interface 26 to send and receive commands to pacemakers 12 and 14 via external device 20. A clinician may use user interface 26 to specify one or more sensing control parameters for sensing cardiac electrical and/or mechanical events corresponding to atrial depolarization and contraction and corresponding to ventricular depolarization and contraction. Typically, user interface 26 includes one or more input devices and one or more output devices, including display unit 24. The input devices of user interface 26 may include a communication device such as a network interface, keyboard, pointing device, voice responsive system, video camera, biometric detection/response system, button, sensor, mobile device, control pad, microphone, presence-sensitive screen, touch-sensitive screen (which may be included in display unit 24), network, or any other type of device for detecting input from a human or machine.

The one or more output devices of user interface 26 may include a communication unit such as a network interface, display, sound card, video graphics adapter card, speaker, presence-sensitive screen, one or more USB interfaces, video and/or audio output interfaces, or any other type of device capable of generating tactile, audio, video, or other output. Display unit 24 may function as an input and/or output device using technologies including liquid crystal displays (LCD), quantum dot display, dot matrix displays, light emitting diode (LED) displays, organic light-emitting diode (OLED) displays, cathode ray tube (CRT) displays, e-ink, or monochrome, color, or any other type of display capable of generating tactile, audio, and/or visual output. In other examples, user interface 26 may produce an output to a user in another fashion, such as via a sound card, video graphics adapter card, speaker, presence-sensitive screen, touch-sensitive screen, one or more USB interfaces, video and/or audio output interfaces, or any other type of device capable of generating tactile, audio, video, or other output. In some examples, display unit 24 is a presence-sensitive display that may serve as a user interface device that operates both as one or more input devices and one or more output devices.

Telemetry unit 28 includes a transceiver and antenna configured for bidirectional communication with a telemetry circuit included in RV pacemaker 12 and a telemetry circuit included in atrial pacemaker 14 and is configured to operate in conjunction with processor 22 for sending and receiving data relating to pacemaker functions via respective communication links 30 and 32. Communication link 30 or 32 may be established between the respective pacemaker 12 or 14 and external device 20 using a radio frequency (RF) link such as BLUETOOTH®, Wi-Fi, or Medical Implant Communication Service (MICS) or other RF or communication frequency bandwidth or communication protocols. Data stored or acquired by the pacemaker 12 or 14, including cardiac signals or associated data derived therefrom, results of device diagnostics, and histories of detected rhythm episodes and delivered therapies, may be retrieved from the pacemaker by external device 20 following an interrogation command. External device 20 may retrieve episodes of sensed cardiac electrical and/or mechanical signals from RV pacemaker 12 and/or atrial pacemaker 14.

Figure 2:
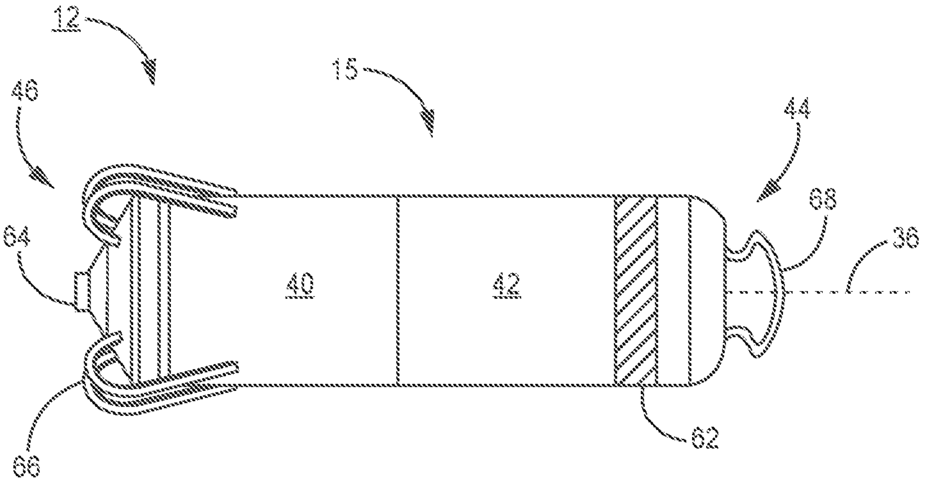
FIG. 2 is a conceptual diagram of the ventricular pacemaker shown in FIG. 1 according to one example.

FIG. 2 is a conceptual diagram of RV pacemaker 12 shown in FIG. 1 according to one example. RV pacemaker 12 includes electrodes 62 and 64 spaced apart along the housing 15 of RV pacemaker 12 for sensing cardiac electrical signals and delivering pacing pulses. Electrode 64 is shown as a tip electrode extending from a distal end 46 of RV pacemaker 12, and electrode 62 is shown as a ring electrode circumscribing a mid-portion of housing 15, adjacent proximal end 44 in this example. Distal end 46 is referred to as "distal" in that it is expected to be the leading end as RV pacemaker 12 is advanced through a delivery tool, such as a catheter, and placed against a targeted implant site.

Electrodes 62 and 64 form an anode and cathode pair for bipolar cardiac pacing and sensing. In alternative embodiments, RV pacemaker 12 may include two or more ring electrodes, two tip electrodes, and/or other types of electrodes exposed along pacemaker housing 15 for delivering electrical stimulation to heart 8 and sensing cardiac electrical signals. Electrodes 62 and 64 may be, without limitation, titanium, platinum, iridium or alloys thereof and may include a low polarizing coating, such as titanium nitride, iridium oxide, ruthenium oxide, platinum black, among others. Electrodes 62 and 64 may be positioned at locations along RV pacemaker 12 other than the locations shown.

Housing 15 is formed from a biocompatible material, such as a stainless steel or titanium alloy. In some examples, the housing 15 may include an insulating coating. Examples of insulating coatings include parylene, urethane, PEEK, or polyimide, among others. The entirety of the housing 15 may be insulated, but only electrodes 62 and 64 uninsulated. Electrode 64 may serve as a cathode electrode and be coupled to internal circuitry, e.g., a pacing pulse generator and cardiac electrical signal sensing circuitry, enclosed by housing 15 via an electrical feedthrough crossing housing 15. Electrode 62 may be formed as a conductive portion of housing 15 defining a ring electrode that is electrically isolated from the other portions of the housing 15 as generally shown in FIG. 2. In other examples, the entire periphery of the housing 15 may function as an electrode that is electrically isolated from tip electrode 64, instead of providing a localized ring electrode such as electrode 62. Electrode 62 formed along an electrically conductive portion of housing 15 serves as a return anode during pacing and sensing.

The housing 15 may include a control electronics subassembly 40 and a battery subassembly 42, which provides power to the control electronics subassembly 40. Control electronics subassembly 42 houses the electronics for sensing cardiac signals, producing pacing pulses and controlling therapy delivery and other functions of RV pacemaker 12. A motion sensor may be implemented as an accelerometer enclosed within housing 15 in some examples. The accelerometer provides a signal to a processor included in control electronics subassembly 40 for signal processing and analysis for detecting cardiac mechanical event signals, e.g., atrial event signals, for use in timing ventricular pacing pulses in synchrony with atrial events to provide atrial synchronous ventricular pacing. Additionally or alternatively, the processor may process acceleration signals produced by the accelerometer due to patient physical activity for providing rate response pacing and may process acceleration signals for determining patient posture.

The accelerometer may be a one-dimensional accelerometer used to obtain a motion signal from which cardiac mechanical events are detected by processing circuitry enclosed by housing 15. In other examples, a two- or three-dimensional accelerometer or other multi-dimensional accelerometer may be used. Each axis of the accelerometer generates an acceleration signal in a different dimension. For instance, in a three-axis or three-dimensional accelerometer, the accelerometer may have one "longitudinal" axis that is parallel to or aligned with the longitudinal axis 36 of RV pacemaker 12 and two orthogonal axes that extend in radial directions relative to the longitudinal axis 36. Practice of the techniques disclosed herein, however, are not limited to a particular orientation of the accelerometer within or along housing 15 or a particular number of axes. Orthogonal arrangement of the elements of a multi-axis accelerometer is not necessarily required.

Each axis of a single or multi-dimensional accelerometer may be defined by a piezoelectric element, micro-electrical mechanical system (MEMS) device or other sensor element capable of producing an electrical signal in response to changes in acceleration imparted on the sensor element, e.g., by converting the acceleration to a force or displacement that is converted to the electrical signal. Each sensor element or axis may be individually or collectively powered to produce an acceleration signal corresponding to a vector aligned with the axis of the sensor element. A vector signal of a multi-dimensional accelerometer (also referred to herein as a "multi-axis" accelerometer) for use in sensing cardiac mechanical events may be selected as a single axis signal or a combination of two or more axis signals. For example, one, two or all three axis signals produced by a three dimensional accelerometer may be selected and combined for processing and analysis for use in detecting an atrial event signal and scheduling a ventricular pacing pulse at an AV delay interval from the atrial event signal. Various methods for detecting an atrial event signal from an accelerometer signal by a ventricular pacemaker for controlling atrial synchronized ventricular pacing are generally disclosed in U.S. Pat. No. 9,399,140 (Cho, et al.), U.S. Pat. No. 10,449,366 (Splett, et al.), U.S. Pat. No. 10,532,212 (Splett, et al.), U.S. patent application Ser. No. 16/703,047, and U.S. patent application Ser. No. 16/703,320 (Splett, et al.), all of which are incorporated herein by reference in their entirety.

RV pacemaker 12 may include features for facilitating deployment and fixation of pacemaker 12 at an implant site. For example, RV pacemaker 12 may include a set of fixation tines 66 to secure RV pacemaker 12 to patient tissue, e.g., by actively engaging with the atrial endocardium and/or interacting with the ventricular trabeculae. Fixation tines 66 are configured to anchor RV pacemaker 12 to position electrode 64 in operative proximity to a targeted tissue for delivering therapeutic electrical stimulation pulses. Numerous types of active and/or passive fixation members may be employed for anchoring or stabilizing pacemaker 12 in an implant position. RV pacemaker 12 may optionally include a delivery tool interface 68. Delivery tool interface 66 may be located at the proximal end 44 of RV pacemaker 12 and is configured to connect to a delivery device, such as a catheter, used to position pacemaker 12 at an implant location during an implantation procedure, for example within a ventricular chamber.

Figure 3:
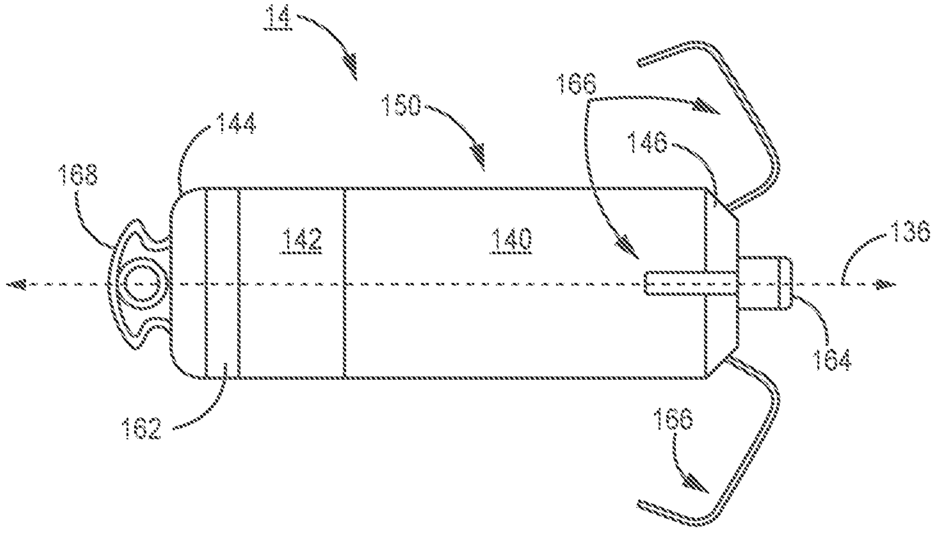
FIG. 3 is a conceptual diagram of the atrial pacemaker shown in FIG. 1.

FIG. 3 is a conceptual diagram of atrial pacemaker 14 configured for implantation in an atrial chamber as shown in FIG. 1. Atrial pacemaker 14 may include a housing-based distal tip electrode 164 on the distal end 146 of housing 150 and a proximal ring electrode 162, adjacent housing proximal end 144. Electrodes 164 and 162 form a cathode and anode pair for sensing cardiac electrical signals from within the RA and delivering atrial pacing pulses. Atrial pacemaker 14 includes housing 150 enclosing circuitry configured to perform the functions attributed to atrial pacemaker 14 herein. Housing 150 may include a control electronics subassembly 140 and a battery subassembly 142 for providing power to circuitry enclosed in control electronics subassembly 140.

Atrial pacemaker 14 may include an accelerometer which may be a single axis or multi-axis accelerometer. In some examples, a three-dimensional accelerometer is enclosed by housing 150 with one accelerometer axis element aligned with longitudinal axis 136. One, two or all three axis signals may be selected by processing circuitry enclosed by housing 15 for sensing cardiac mechanical event signals and/or sense acceleration signals associated with patient physical activity, e.g., for providing rate response pacing, and/or for determining patient posture. In particular, atrial pacemaker 14 may be configured to determine a ventricular activity metric correlated to the frequency and/or timing of far field ventricular mechanical events in the atrial accelerometer signal for use in determining one or more AV synchrony metrics for assessing the performance of RV pacemaker 12 in delivering atrial synchronized ventricular pacing.

Atrial pacemaker 14 may include fixation tines 166 to secure pacemaker 14 to patient tissue, e.g., by actively engaging with the atrial endocardium and/or interacting with the atrial pectinate muscle. Fixation tines 166 are configured to anchor atrial pacemaker 14 to position electrode 164 in operative proximity to a targeted tissue for delivering therapeutic electrical stimulation pulses. Atrial pacemaker 14 may optionally include a delivery tool interface 168. Delivery tool interface 168 may be located at the proximal end 144 of pacemaker 14 and is configured to connect to a delivery device, such as a catheter, used to position pacemaker 14 at an implant location during an implantation procedure, for example within and atrial chamber.

The size of housing 150 and the size, shape and location of fixation tines 166 and electrodes 162 and 164 may be adapted for use in an atrial implant location as needed compared to housing 15, fixation times 66 and/or electrodes 62 and 64 of RV pacemaker 12, configured for use in a ventricular chamber. In some examples, RV pacemaker 12 and atrial pacemaker 14 may be analogous in physical structure but control electronics assemblies 40 and 140 may include hardware, firmware and/or software configured to perform sensing and pacing functions according to their respective implant locations.

Figure 4:
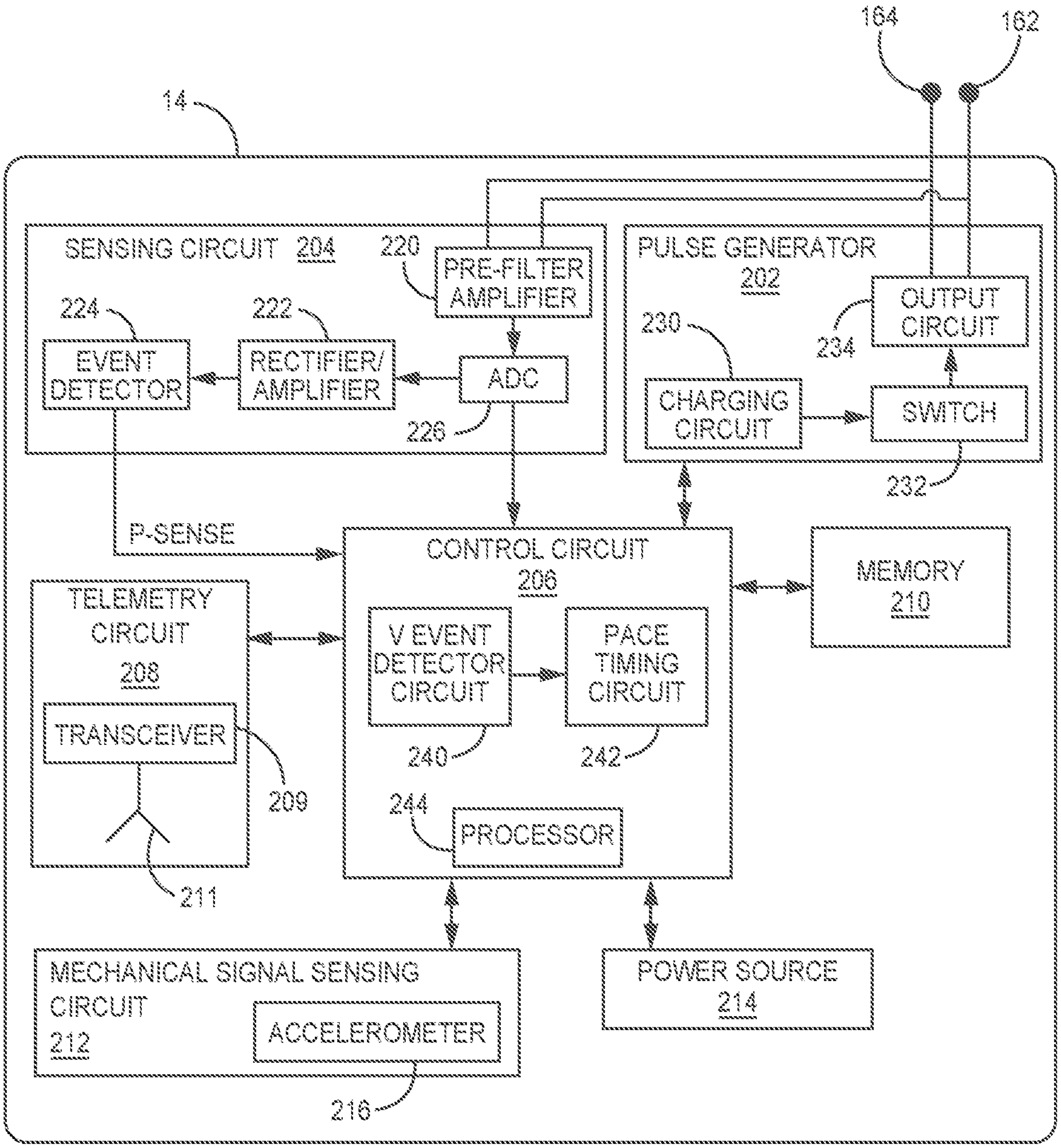
FIG. 4 is a conceptual diagram of an example configuration of the atrial pacemaker shown in FIG. 1.

FIG. 4 is a conceptual diagram of an example configuration of atrial pacemaker 14 shown in FIG. 1. FIG. 4 is described in the context of atrial pacemaker 14 of FIG. 1 as an example of a medical device configured to sense cardiac signals including far field ventricular event signals for use in determining at least one AV synchrony metric for assessing the performance of ventricular pacemaker 12 in maintaining AV synchrony. At least some of the circuitry and components and the associated functionality described in conjunction with FIG. 4 may generally correspond to circuitry incorporated in RV pacemaker 12 and adapted for use in sensing cardiac signals from within the RV and for generating ventricular pacing pulses, in particular atrial-synchronized ventricular pacing pulses, e.g., according to any of the above-incorporated references.

Furthermore, it is to be understood that sensing and processing circuitry generally described in conjunction with FIG. 4 for performing the functions of sensing a cardiac electrical signal and/or cardiac mechanical signal that includes far field ventricular event signals for use in determining ventricular activity metrics and AV synchrony metrics therefrom may be included in, or adapted for use in, other medical devices such as an extra-cardiac or non-transvenous ICD or a cardiac monitor as described above. Atrial pacemaker 14 is described herein for the sake of illustration and convenience as one medical device that may sense cardiac signals including far field ventricular event signals and is configured to determine an AV synchrony metric. The disclosed techniques are not intended to be limited to implementation only in an atrial pacemaker, however. Aspects of the disclosed techniques may be implemented in a variety of medical devices, which may be implantable, wearable or external devices, configured to sense or receive a cardiac signal including far field ventricular event signals.

Atrial pacemaker 14 includes a pulse generator 202, a cardiac electrical signal sensing circuit 204, a control circuit 206, memory 210, telemetry circuit 208, cardiac mechanical signal sensing circuit 212 and a power source 214. The various circuits represented in FIG. 4 may be combined on one or more integrated circuit boards which include an application specific integrated circuit (ASIC), an electronic circuit, a processor (shared, dedicated, or group) and memory that execute one or more software or firmware programs, a combinational logic circuit, state machine or other suitable components that provide the described functionality.

Cardiac mechanical signal sensing circuit 212 includes an accelerometer 216 in the examples described herein for sensing far field ventricular mechanical event signals, which may be used by a processor 244 of control circuit 206 for determining at least one AV synchrony metric. In some examples, the accelerometer 216 may be included in mechanical signal sensing circuit 212 or on or in housing 150 and coupled to cardiac mechanical signal sensing circuit 212. Cardiac mechanical signal sensing circuit 212 is not limited to including an accelerometer, however, and other sensors of mechanical cardiac events, such as pressure sensors, flow sensors, acoustical sensors or the like may be utilized successfully in atrial pacemaker 14 for sensing cardiac mechanical event signals, including far field ventricular event signals, for use according to the techniques described herein for assessing AV synchrony.

Cardiac mechanical signal sensing circuit 212 may pass an accelerometer signal, which may correspond to one or more accelerometer axis signals, to control circuit 206 for processing and analysis, individually or in combination for detecting cardiac mechanical events. The accelerometer 216 of cardiac mechanical signal sensing circuit 212 produces an electrical signal correlated to motion or vibration of sensor accelerometer 216 (and atrial pacemaker 14), e.g., when subjected to flowing blood and cardiac motion (as well as patient body motion). The cardiac mechanical signal sensing circuit 212 may include one or more filter, amplifier, rectifier, analog-to-digital converter (ADC) and/or other components for producing a signal that is passed to control circuit 206 for further processing and analysis. For example, each vector signal produced by each individual axis of a multi-axis accelerometer may be filtered by a high pass filter, e.g., a 10 Hz high pass filter, or a bandpass filter, e.g., a 10 Hz to 30 Hz bandpass filter. The filtered signal may be digitized by an ADC and rectified for use by ventricular (V) event detector circuit 240 for detecting far field ventricular event signals. The high pass filter may be raised (e.g., to 15 Hz) if needed to detect far field ventricular event signals that have higher frequency content. In some examples, high pass filtering is performed with no low pass filtering. In other examples, each accelerometer axis signal is filtered by a low pass filter, e.g., a 30 Hz low pass filter, with or without high pass filtering. A bandpass filtered acceleration signal from one or more of the accelerometer axes may be passed to ventricular event detector circuit 240 for detecting far field ventricular mechanical events, or more generally for determining a ventricular activity metric, from the accelerometer signal, which may be determined over multiple atrial cycles, for assessing AV synchrony. Various signal processing and analysis techniques may be used for detecting far field ventricular event signals, such as fast Fourier transform, determining a differential signal, or determining a number of threshold crossings by the acceleration signal where the threshold may be greater than or less than the amplitude of atrial event signals, as examples.

In some examples, a signal from at least one axis of accelerometer 216 may be passed to control circuit 206 for determining patient posture and/or a patient physical activity metric in addition to using the accelerometer signal for detecting far field ventricular events for assessing AV synchrony. Acceleration forces on the accelerometer 216 occur due to patient posture changes relative to gravitational acceleration forces and due to patient motion during physical activity, such as exercise and activities of daily living. The accelerometer axis signal(s) may be used for determining patient posture by control circuit 206. In some examples, control circuit 206 is configured to discriminate between a horizontal or non-upright position and non-horizontal or upright positions and may discriminate between various non-upright postures such as a left side-lying position, a right side-lying position, a prone position and/or a supine position.

Patient posture may be determined by control circuit 206 from one or more accelerometer axis signals for determining AV synchrony metrics during different patient postures, e.g., upright vs. non-upright, side-lying vs. supine positions or the like. Control circuit 206 may detect a patient posture from the accelerometer axis signals and store sensed ventricular event data in memory 210 in conjunction with different detected patient postures, for example, so that an AV synchrony metric may be determined for at least two different patient postures. In some examples, a change in patient posture may be detected from an accelerometer signal for use in controlling when control circuit 206 determines an AV synchrony metric. As described below in conjunction with FIG. 12, when control circuit 206 determines AV asynchrony, control circuit 206 may delay re-determining an AV synchrony metric until a change in patient posture is detected, for example.

A patient physical activity metric correlated to the level of physical exertion and metabolic demand of the patient may be determined from the accelerometer signal. The patient activity metric, sometimes referred to as an "activity count," may be used by control circuit 206 to separate ventricular events sensed during different patient activity levels to enable the AV synchrony metric(s) to be determined during different levels of patient activity in some examples.

Control circuit 206 may determine the patient activity metric for determining a sensor indicated pacing rate (SIR) for providing rate response pacing during increased patient activity in some examples. The accelerometer axis signal(s) used for determining a patient activity metric may be filtered differently than the accelerometer axis signals used for sensing ventricular events or determining a ventricular activity metric and for assessing AV synchrony. For example, cardiac mechanical signal sensing circuit 212 may include a low pass filter having an upper cutoff frequency of 10 Hz for passing a low pass filtered patient activity signal to processor 244 for determining a patient activity metric.

The patient activity metric may be determined by control circuit 206 at a desired frequency, e.g., every two seconds, for use in determining an SIR that meets the metabolic requirements of the patient based on physical activity. The SIR may vary between the programmed minimum lower rate during periods of rest (minimal activity metric) and a maximum upper pacing rate during periods of maximum exertion. The SIR may be determined according to an SIR transfer function, which may include different rates of change of the SIR over different ranges of the patient activity metric. Control circuit 206 may control pulse generator 202 to deliver rate response atrial pacing according to the SIR.

In some examples, the patient activity metric is determined as an activity count. In these instances, control circuit 206 includes a counter to track the activity count as the number of times the accelerometer signal crosses a threshold amplitude during an activity count interval, for example a 2-second interval. The count at the end of each activity count interval is correlated to patient body motion during the activity count interval and is therefore correlated to patient metabolic demand. Example methods for obtaining an activity count over an n-second interval are generally disclosed in U.S. Pat. No. 5,720,769 (van Oort), incorporated herein by reference in its entirety.

In other examples, an activity metric may be obtained from the patient physical activity signal by integrating or summing activity signal sample points over an activity count interval, e.g., a two-second interval though longer or shorter intervals of time may be used for determining the activity metric. The activity metric may be converted to a target heart rate determined as the SIR based on an SIR transfer function that includes a lower rate set point and an activity of daily living (ADL) range and a maximum upper rate. Examples of methods for determining an SIR based on an activity metric and for establishing an SIR transfer function applied to patient activity metrics determined from an intracardiac motion signal are generally disclosed in U.S. Pat. No. 9,724,518 (Sheldon, et al.), incorporated herein by reference in its entirety.

One example of an accelerometer for use in implantable medical devices that may be implemented in conjunction with the techniques disclosed herein is generally disclosed in U.S. Pat. No. 5,885,471 (Ruben, et al.), incorporated herein by reference in its entirety. An implantable medical device arrangement including a piezoelectric accelerometer for detecting patient motion is disclosed, for example, in U.S. Pat. No. 4,485,813 (Anderson, et al.) and U.S. Pat. No. 5,052,388 (Sivula, et al.), both of which patents are hereby incorporated by reference herein in their entirety. Examples of three-dimensional accelerometers that may be implemented in atrial pacemaker 14 and used for detecting cardiac mechanical events using the presently disclosed techniques are generally described in U.S. Pat. No. 5,593,431 (Sheldon) and U.S. Pat. No. 6,044,297 (Sheldon), both of which are incorporated herein by reference in their entirety. Other accelerometer designs may be used for producing an electrical signal that is correlated to acceleration forces imparted on atrial pacemaker 14 due to atrial and far field ventricular mechanical events.

Cardiac electrical signal sensing circuit 204 is configured to receive at least one cardiac electrical signal via electrodes coupled to atrial pacemaker 14, e.g., electrodes 162 and 164. The cardiac electrical signal is received by a pre-filter and amplifier circuit 220. Pre-filter and amplifier circuit 220 may include a high pass filter to remove DC offset, e.g., a 2.5 to 5 Hz high pass filter, or a wideband filter having a bandpass of 2.5 Hz to 100 Hz or narrower to remove DC offset and high frequency noise. Pre-filter and amplifier circuit 220 may further include an amplifier to amplify the “raw” cardiac electrical signal passed to analog-to-digital converter (ADC) 226. ADC 226 may pass a multi-bit, digital electrogram (EGM) signal to control circuit 206 for use by ventricular event detector circuit 240 in identifying ventricular electrical events, e.g., FFRWs. FFRWs may be sensed by cardiac electrical signal sensing circuit 204 or ventricular event detector circuit 240 for use in determining an AV synchrony metric, instead of or in combination with ventricular mechanical events sensed from the accelerometer signal. Identification of FFRWs may be used in confirming far field ventricular events sensed from the accelerometer signal. Atrial events, e.g., P-waves, sensed by sensing circuit 204 may be used in setting blanking periods and/or windows for detecting far field ventricular events from the accelerometer signal, comparing an atrial rate to a ventricular event rate, and/or normalizing a ventricular activity metric for determining at least one AV synchrony metric as described below in conjunction with the accompanying diagrams and flow charts. The digital signal from ADC 226 may be passed to rectifier and amplifier circuit 222, which may include a rectifier, bandpass filter, and amplifier for passing a rectified atrial signal to cardiac event detector 224.

Cardiac event detector 224 may include a sense amplifier or other detection circuitry that compares the incoming rectified, cardiac electrical signal to a cardiac event sensing threshold, which may be an auto-adjusting threshold. For example, when the incoming signal crosses a P-wave sensing threshold, the cardiac event detector 224 produces an atrial sensed event signal (labeled “P-sense”) that is passed to control circuit 206. In other examples, cardiac event detector 224 may receive the digital output of ADC 226 for detecting P-waves by a comparator, morphological signal analysis of the digital EGM signal or other P-wave detection techniques.

Control circuit processor 244 may provide sensing control signals to sensing circuit 204, e.g., P-wave sensing threshold, sensitivity, and various blanking and refractory intervals applied to the cardiac electrical signal for controlling P-wave sensing. P-wave sensed event signals passed from cardiac event detector 224 to control circuit 206 may be used for scheduling atrial pacing pulses by pace timing circuit 242 and for use in setting windows and/or blanking periods for detecting ventricular events by ventricular event detector circuit 240 or for determining a ventricular activity metric from the accelerometer signal and/or the EGM signal. P-wave sensed event signals may be used by control circuit 206 for identifying multiple atrial cycles over which a ventricular activity metric is determined for use in determining an AV synchrony metric, for example.

As indicated above, cardiac event detector 224 may be configured to sense FFRWs from the atrial signal received by electrodes 162 and 164. FFRWs may be sensed based on an R-wave sensing threshold crossing, which may occur after an atrial pacing pulse or sensed P-wave. In other examples, control circuit 206 may detect FFRWs from the digital EGM signal passed to ventricular (V) event detector circuit 240 from ADC 226. FFRWs may be detected based on a morphological analysis of the atrial EGM signal and/or based on an FFRW sensing threshold amplitude crossing by the atrial EGM signal. Cardiac electrical signal sensing circuit 204 may include a P-wave sensing channel and an FFRW sensing channel in some examples. Components included in the P-wave sensing channel and the FFRW sensing channel may be shared between both channels in some examples. For example, pre-filter/amplifier 220 and ADC 226 may be shared by both channels with the output of ADC 226 being passed separately to a P-wave detector and to an FFRW detector included in event detector 224. Different filtering and amplification may be applied to the output of ADC 226 before passing the signal to the respective P-wave detector and FFRW detector.

Control circuit 206 includes a ventricular event detector circuit 240, pace timing circuit 242, and processor 244. Control circuit 206 may receive P-wave sensed event signals, FFRW sensed event signals, and/or digital cardiac electrical signals from sensing circuit 204 for use in detecting and confirming cardiac events, controlling atrial pacing and for determining at least one AV synchrony metric. Ventricular event detector circuit 240 may be configured to detect ventricular events from a signal received from accelerometer 216 in some examples. In some examples, ventricular event detector circuit 240 may start a ventricular event sensing window in response to identifying an atrial event, e.g., a P-wave sensed event signal from sensing circuit 204 or delivery of an atrial pacing pulse by pulse generator 202. The ventricular event sensing window may correspond to a time period after the atrial electrical event during which a far field ventricular event is expected to occur during AV synchrony, when RV pacemaker 12 is delivering ventricular pacing synchronized to atrial events at a programmed AV pacing delay. Ventricular event detector circuit 240 may be configured to determine if the accelerometer signal satisfies far field ventricular event detection criteria during the ventricular event sensing window in some examples.

Control circuit 206 may determine a ventricular activity metric as a count of far field ventricular events detected over multiple atrial cycles according to some examples. Processor 244 may receive ventricular event detection signals from detector circuit 240 for counting the detected far field ventricular events. The count of ventricular events may be determined as a ventricular activity metric, and an AV synchrony metric may be determined by control circuit 206 as the ventricular event count determined as a percentage of all atrial cycles (over a given time interval or since atrial pacemaker implant) in some examples. When RV pacemaker 12 is sensing atrial events and delivering ventricular pacing pulses at a programmed AV delay for maintaining AV synchrony, the rate of atrial events (sensed and paced) determined by atrial pacemaker 14 and the rate of ventricular events detected by atrial pacemaker 14 are expected to be equal. Accordingly, an AV synchrony metric may be a ratio of detected far field ventricular events to atrial events or a rate difference between detected far field ventricular events and atrial events.

Additionally or alternatively, the detected far field ventricular events may be used by control circuit 206 in determining AV intervals for determining an AV synchrony metric. A far field ventricular event may be detected based on sensing a FFRW from the atrial electrical signal. Alternatively a far field ventricular event may be sensed based on a threshold crossing by the accelerometer signal and/or one or more accelerometer signal features during the ventricular event sensing window meeting far field ventricular event sensing criteria, e.g., as described below in conjunction with FIG. 7. An AV interval may be determined by control circuit 206 as the time interval from a detected far field ventricular event to the most recent, preceding sensed P-wave or delivered atrial pacing pulse. When RV pacemaker 12 is maintaining AV synchrony, the AV intervals determined between atrial events and subsequent ventricular events are expected to be consistent with the AV delay programmed in RV pacemaker 12 with little variation. An AV synchrony metric may therefore be determined by control circuit 206 based on ventricular activity metrics determined as AV intervals or a measure of centeredness or variability thereof.

In other examples, control circuit 206 may determine a ventricular activity metric over multiple atrial cycles with or without requiring blanking periods and sensing windows. For instance, as described below in conjunction with FIG. 10, the ventricular activity metric representative of ventricular rate may be determined as an integration metric of the accelerometer signal determined over an integration time interval that includes multiple atrial cycles. Control circuit 206 may determine the AV synchrony metric as the integration metric normalized by the atrial rate or number of atrial cycles during the integration time interval in some examples.

Pace timing circuit 242 may additionally receive cardiac sensed event signals from event detector 224 for use in controlling the timing of pacing pulses delivered by pulse generator 202. Processor 244 may include one or more clocks for generating clock signals that are used by pace timing circuit 242 to time out an atrial pacing interval, e.g., a lower rate pacing interval for treating bradycardia or a temporary lower rate interval for providing rate response pacing according to an SIR based on a patient physical activity metric. The pacing interval, sometimes referred to as an "escape interval," may be restarted by pace timing circuit 242 in response to each atrial electrical event, e.g., upon receipt of each P-wave sensed event signal and upon delivery of each atrial pacing pulse by pulse generator 202.

Pace timing circuit 242 may include one or more pacing rate interval timers or counters used to time out the pacing escape interval. For example, pace timing circuit 242 may include a timer or counter for timing out the atrial pacing interval, which may be a programmable interval stored in memory 210 and retrieved by processor 244. When the escape interval timer expires without a P-wave sensed event signal received from event detector 224, pulse generator 202 generates an atrial pacing pulse delivered to the RA via electrodes 162 and 164. When a P-wave sensed event signal is received from event detector 224 by control circuit 206, the value of the escape interval timer when the P-wave sensed event signal is received may be used by processor 244 for determining PP intervals between consecutive atrial electrical events for determining the atrial rate. Processor 244 may determine RR intervals between consecutive FFRWs sensed by sensing circuit 204, in some examples, for determining the ventricular rate as a ventricular activity metric.

In addition to providing control signals to pace timing circuit 242 and pulse generator 202 for controlling the timing of atrial pacing pulses, processor 244 may retrieve programmable pacing control parameters, such as pacing pulse amplitude and pacing pulse width, which are passed to pulse generator 202 for controlling pacing pulse delivery. Pulse generator 202 may include charging circuit 230, switching circuit 232 and an output circuit 234. Charging circuit 230 is configured to receive current from power source 214 and may include a holding capacitor that may be charged to a pacing pulse amplitude under the control of a voltage regulator included in charging circuit 230. The pacing pulse amplitude may be set based on a control signal from control circuit 206. Switching circuit 232 may control when the holding capacitor of charging circuit 230 is coupled to the output circuit 234 for delivering the pacing pulse. For example, switching circuit 232 may include a switch that is activated by a timing signal received from pace timing circuit 242 upon expiration of a pacing escape interval and kept closed for a programmed pacing pulse width to enable discharging of the holding capacitor of charging circuit 230. The holding capacitor, previously charged to the pacing pulse voltage amplitude, is discharged across electrodes 162 and 164 through the output capacitor of output circuit 234 for the programmed pacing pulse duration, also referred to herein as the pacing pulse "width."

Memory 210 may include computer-readable instructions that, when executed by control circuit 206, cause control circuit 206 to perform various functions attributed throughout this disclosure to atrial pacemaker 14. The computer-readable instructions may be encoded within memory 210. Memory 210 may include any non-transitory, computer-readable storage media including any volatile, non-volatile, magnetic, optical, or electrical media, such as a random access memory (RAM), read-only memory (ROM), non-volatile RAM (NVRAM), electrically-erasable programmable ROM (EEPROM), flash memory, or other digital media with the sole exception being a transitory propagating signal.

Memory 210 may store sensed ventricular event data corresponding to the number and/or timing of ventricular events sensed by ventricular event detector circuit 240 from the signal from mechanical signal sensing circuit 212 and/or corresponding to FFRWs sensed from the cardiac electrical signal by cardiac electrical signal sensing circuit 204. In some examples, memory 210 includes a counter for counting atrial cycles that do not include a sensed ventricular event, which may be counted as AV asynchrony cycles. Additionally or alternatively, memory 210 may include a counter for counting atrial cycles that do include a sensed ventricular event, which may be counted as AV synchrony cycles, which may depend on when the far field ventricular event is sensed during the atrial cycle. Memory 210 may include a buffer for storing sensed ventricular event times relative to a most recent preceding atrial event, sensed or paced, for use in determining AV intervals. Data relating to ventricular events detected from the accelerometer signal and/or the cardiac electrical signal may be buffered in memory 210 for use by processor 244 for determining one or more AV synchrony metrics. AV synchrony data may be output to memory 210 for use in controlling pulse generator 202, transmitting AV synchrony data and/or transmitting an AV asynchrony notification signal, as examples.

Memory 210 may store episodes of cardiac electrical signals sensed by sensing circuit 204 and/or episodes of acceleration signals from mechanical signal sensing circuit 212. Memory 210 may additionally or alternatively store data determined by control circuit 206 relating to sensed cardiac events, from both the cardiac electrical signal and the accelerometer signal, particularly data relating to determination of an AV synchrony metric. For instance, memory 210 may store data from control circuit 206 that can be used by processor 244 or external device processor 22 for determining the percentage of time or percentage of all atrial cycles that AV synchrony is determined and/or the percentage of time or percentage of atrial cycles that AV asynchrony is determined. Poor AV synchrony performance by RV pacemaker 12 may be determined when an AV synchrony metric, e.g., a count or percentage of AV synchronous atrial cycles, is less than a threshold or the ratio of ventricular rate to atrial rates is not 1:1. In another example, poor AV synchrony performance by RV pacemaker 12 may be determined when the average AV interval is greater than an expected AV interval and/or the variability of the AV intervals is greater than a threshold. An episode of the EGM signal passed to control circuit 206 from ADC 226 and/or the accelerometer signal from mechanical signal sensing circuit 212 may be stored in memory 210, e.g., in response to determining AV asynchrony by control circuit 206, for later transmission to external device 20 by telemetry circuit 208.

Control circuit 206 may generate an output based on one or more determined AV synchrony metrics. In some examples, signals and/or data pertaining to AV synchrony are transmitted to external device 20 for generating a display, e.g., as part of a GUI. In some examples, the output may include an alert or notification indicating AV asynchrony is determined. In still other examples, the output may include a signal transmitted to RV pacemaker 12 indicating that AV synchrony criteria are not met to trigger RV pacemaker 12 to adjust an atrial event sensing control parameter and/or adjust a ventricular pacing control parameter.

In some examples, the output generated by control circuit 206 based on an AV synchrony metric may include adjusting the pacing control parameters used by pulse generator 202 for delivering atrial pacing pulses. For instance, when atrial pacing is being delivered, RV pacemaker 12 may oversense atrial pacing pulses as R-waves, causing RV pacemaker 12 to withhold ventricular pacing pulses. Cross-chamber oversensing occurs when pacing pulses delivered in a one heart chamber are falsely sensed as intrinsic events in a different heart chamber. By adjusting the atrial pacing rate, pulse amplitude, and/or pulse width used by pulse generator 202 for delivering atrial pacing pulses, the relative timing and/or signal strength of the atrial pacing pulse artifact in a signal sensed by RV pacemaker 12 may change. Even small changes in timing and or size of atrial pacing artifact in a signal sensed by the RV pacemaker 12 may reduce cross-chamber oversensing and thereby enable RV pacemaker 12 to restore atrial synchronized ventricular pacing.

Telemetry circuit 208 includes a transceiver 209 and antenna 211 for transferring and receiving data via a radio frequency (RF) communication link. Telemetry circuit 208 may be capable of bi-directional communication with external device 20 (FIG. 1) as described above. Cardiac mechanical signals and cardiac electrical signals, and/or data derived therefrom may be transmitted by telemetry circuit 208 to external device 20. Programmable control parameters and algorithms for sensing cardiac events, including P-waves and in some examples FFRWs, from the atrial electrical signal, sensing ventricular events from the accelerometer signal, and for controlling pacing therapies delivered by pulse generator 202 may be received by telemetry circuit 208 and stored in memory 210 for access by control circuit 206.

Power source 214 provides power to each of the other circuits and components of atrial pacemaker 14 as required. Power source 214 may include one or more energy storage devices, such as one or more rechargeable or non-rechargeable batteries. The connections between power source 214 and other pacemaker circuits and components are not shown in FIG. 4 for the sake of clarity but are to be understood from the general block diagram of FIG. 4. For example, power source 214 may provide power as needed to charging and switching circuitry included in pulse generator 202; amplifiers, ADC 226 and other components of sensing circuit 204; telemetry circuit 208; memory 210 and mechanical signal sensing circuit 212 including accelerometer 216.

The functions attributed to atrial pacemaker 14 herein may be implemented in one or more processors, controllers, hardware, firmware, software, or any combination thereof. Depiction of different features as specific circuitry is intended to highlight different functional aspects and does not necessarily imply that such functions must be realized by separate hardware, firmware and/or software components or by any particular circuit architecture. Rather, functionality associated with one or more circuits described herein may be performed by separate hardware, firmware and/or software components, or integrated within common hardware, firmware and/or software components. For example, detection of far field ventricular events, or more generally determination of a ventricular activity metric, and determination of an AV synchrony metric may be implemented in control circuit 206 executing instructions stored in memory 210 and relying on input from cardiac electrical signal sensing circuit 204 and/or mechanical signal sensing circuit 212. Providing software, hardware, and/or firmware to accomplish the described functionality in the context of any modem medical device, given the disclosure herein, is within the abilities of one of skill in the art.

Figure 5:
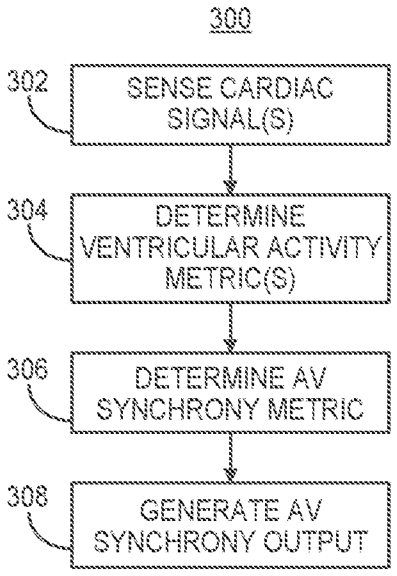
FIG. 5 is a flow chart of a method that may be performed by a medical device for determining an AV synchrony metric according to techniques disclosed herein.

FIG. 5 is a flow chart 300 of a method that may be performed by a medical device for determining an AV synchrony metric according to techniques disclosed herein. The AV synchrony metric is a device diagnostic metric that may be used for assessing the performance of RV pacemaker 12 in delivering atrial synchronized ventricular pacing in some examples. A variety of factors may affect the performance of RV pacemaker 12 in maintaining AV synchrony. In some examples, RV pacemaker 12 may be configured to sense an atrial event from within the ventricle for triggering delivery of a ventricular pacing pulse at an AV delay. The performance of RV pacemaker 12 in maintaining AV synchrony depends in part on the reliability of atrial event sensing from a ventricular implant location. The atrial events may be sensed by RV pacemaker 12 as far field P-waves sensed from the cardiac electrical signal received by the cardiac electrical signal sensing circuit of RV pacemaker 12 (analogous to the cardiac electrical signal sensing circuit 204 of atrial pacemaker 14 described above, but in RV pacemaker 12 the sensing circuit is configured for sensing R-waves and, in some examples, far field P-waves).

In other examples, the atrial event may be sensed by RV pacemaker 12 as the atrial mechanical event due to atrial contraction sensed from a cardiac mechanical signal. RV pacemaker 12 may include a cardiac mechanical signal sensing circuit including an accelerometer analogous to mechanical signal sensing circuit 212 described above in conjunction with FIG. 4. RV pacemaker 12 may be configured to sense atrial events from the accelerometer signal sensed within the RV and schedule a ventricular pacing pulse at an AV delay from the sensed atrial event. The performance of RV pacemaker 12 in maintaining AV synchrony depends at least in part on the reliability and accuracy of sensing atrial events from a cardiac electrical or mechanical signal sensed from a ventricular location. When atrial events are reliably sensed beat by beat, RV pacemaker 12 is able to reliably deliver ventricular pacing pulses at a programmed AV delay. When atrial events are undersensed or oversensed, however, ventricular pacing pulses may be delivered asynchronously with the atrial events. The ventricular pacing pulses do not track the atrial events at a consistent rate and/or AV delay.

The performance of RV pacemaker 12 in maintaining AV synchrony may also be affected by the reliability of R-wave sensing by RV pacemaker 12. RV pacemaker 12 inhibits a scheduled ventricular pacing pulse in response to an R-wave sensed before the pacing interval expires. In some instances, cross-chamber oversensing may occur when atrial pacing pulses delivered by atrial pacemaker 14 are falsely sensed as R-waves by RV pacemaker 12. In other instances, non-cardiac noise due to electromagnetic interference or other noise artifact may be falsely sensed as R-waves causing ventricular pacing pulses to be withheld. At other times, R-waves may be undersensed, which could lead to ventricular pacing pulses being delivered at times during the cardiac cycle that interferes with sensing of atrial events, resulting in AV asynchrony.

Accordingly, atrial pacemaker 14 may be configured to sense a cardiac signal at block 302 for use in determining an AV synchrony metric as a device-related diagnostic for assessing the performance of RV pacemaker 12 in maintaining AV synchrony. At block 304, control circuit 206 may determine one or more ventricular activity metrics from the cardiac signal(s) sensed at block 302 for use in determining an AV synchrony metric at block 306. The ventricular activity metric is representative of the ventricular rate and/or AV interval(s).

In some examples, atrial pacemaker 14 may sense an atrial electrical signal at block 302 for sensing FFRWs for use in determining a ventricular activity metric at block 304. In other examples, atrial pacemaker 14 may sense an atrial mechanical signal at block 302 that includes far field ventricular event signals corresponding to ventricular mechanical activity for determining a ventricular activity metric at block 304. As described below, the ventricular activity metric determined at block 304 may be a count of atrial cycles that include a sensed far field ventricular event. The AV synchrony metric determined at block 306 may be a percentage of all atrial cycles that include a sensed far field ventricular event based on the count determined at block 304. More specifically, the AV synchrony metric may be a percentage of atrial cycles that include a far field ventricular event sensed within an expected AV interval in some examples.

In other examples, the ventricular activity metric may be determined over multiple atrial cycles without requiring sensing of far field ventricular events beat by beat. For example, as described below, a ventricular activity metric may be an integration metric determined from the accelerometer signal at block 304 by summing sample point amplitudes of the accelerometer signal. The integration metric is therefore correlated to the ventricular rate. When the integration metric is determined from the atrial signal only during ventricular event sensing windows following atrial events, the integration metric is representative of the far field ventricular events that are synchronized to atrial events. The AV synchrony metric may be determined at block 306 as the integration metric divided by the number of atrial events during the integration time interval to provide a normalized integration metric that is correlated to a ratio of ventricular activity to atrial activity.

A variety of AV synchrony metrics may be determined from one or more cardiac signals sensed from a non-ventricular location, remotely from the ventricles, based on determining metrics of far field ventricular events present in the sensed cardiac signal(s). In this way, an independent signal that is not sensed by the RV pacemaker 12 may be used to determine the AV synchrony metric to assess the performance of RV pacemaker 12 in maintaining AV synchrony. The cardiac signal(s) used to determine the AV synchrony metric may be sensed from outside the ventricles and even from outside the heart in some examples. The AV synchrony metric may be independent of whether the patient is experiencing AV block or intrinsic AV conduction since the atrial pacemaker 14 may determine ventricular activity metrics at block 304 that may include both paced and intrinsic ventricular events, and may not differentiate or discriminate between paced and intrinsic ventricular events. In this way, the performance of RV pacemaker 12 in delivering atrial synchronized ventricular pacing may be assessed independent of its own sensing performance.

While flow chart 300 is described in conjunction with atrial pacemaker 14, it is to be understood that processor 22 of external device 20 may perform some or all of the processing of the cardiac signal(s) sensed by atrial pacemaker 14 for determining an AV synchrony metric. External device processor 22 may obtain cardiac signal episodes transmitted from atrial pacemaker 14 for determining ventricular activity metrics and AV synchrony metrics based on the ventricular activity metrics. In other examples, atrial pacemaker 14 may determine ventricular activity metrics, e.g., counts of far field ventricular sensed events, histograms of AV intervals, and/or acceleration signal integration metrics, and transmit the ventricular activity metrics to external device processor 22. External device processor 22 may determine the AV synchrony metric from data received from atrial pacemaker 14. Accordingly, the processing and analysis techniques disclosed herein for determining an AV synchrony metric may be determined by a processor of an implanted medical device configured to sense at least one cardiac signal from a non-ventricular position or by a processor of an external device configured to obtain cardiac signal(s) and/or ventricular event data from the implanted medical device configured to sense the cardiac signal(s), e.g., from atrial pacemaker 14.

At block 308, control circuit 206 of atrial pacemaker 14 (and/or external device processor 22) may generate an output in response to the determined AV synchrony metric(s). In some examples, control circuit 206 outputs AV synchrony metric data to memory 210 to be stored for subsequent transmission by telemetry circuit 208. External device processor 22 may receive AV synchrony metric data (via telemetry unit 28) and may generate a representation of the AV synchrony metric data for display by display unit 54, which may be displayed in a GUI. In other examples, control circuit 206 may generate an output at block 308 that includes an adjustment to an atrial pacing control parameter. An adjustment to the atrial pacing rate, atrial pacing pulse amplitude and/or atrial pacing pulse width may enable RV pacemaker 12 to regain reliable atrial event sensing and/or R-wave sensing for controlling ventricular pacing synchronized to atrial events at the programmed AV delay. In other examples, the output generated at block 308 may include a signal transmitted by atrial pacemaker 14 indicating that AV asynchrony is determined. RV pacemaker 12 may receive the transmitted signal and perform one or more adjustments to one or more sensing control parameters and/or ventricular pacing control parameters in order to promote restored AV synchrony.

Figure 6:
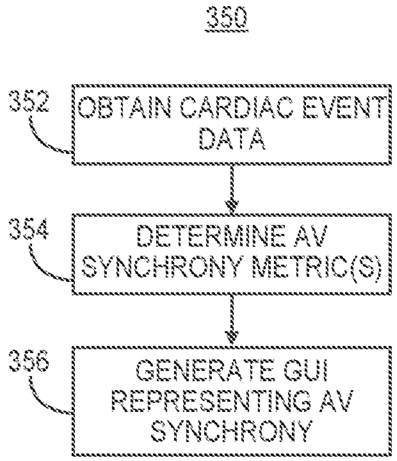
FIG. 6 is a flow chart of a method that may be performed by a processor of a medical device for generating data for a user interface according to some examples.

FIG. 6 is a flow chart 350 of a method that may be performed by a processor of a medical device according to some examples. As indicated above, processor 22 of external device 20 may receive one or more cardiac signals transmitted from atrial pacemaker 14 for use in determining ventricular activity metrics for determining an AV synchrony metric. Additionally or alternatively, atrial pacemaker 14 may determine ventricular activity metrics from the atrial electrical signal and/or atrial mechanical signal and transmit the ventricular activity metric data, along with atrial sensed event and/or atrial pacing data, to external device 20. In this way, external device processor 22 may obtain cardiac event data at block 352. In some examples, processor 22 may obtain cardiac event data in the form of histogram data stored in atrial pacemaker memory 210 as further described below. For instance, atrial pacemaker 14 may increase a histogram bin count for each far field ventricular event sensed from the atrial electrical or atrial mechanical event signal. In some examples, the histogram bins may be allocated for counting far field ventricular events sensed following atrial sensed events and far field ventricular events following atrial pacing pulses. One histogram bin stores a count of ventricular events sensed following an immediately preceding an atrial event that is a sensed P-wave. A second histogram bin stores a count of ventricular events sensed following an immediately preceding atrial event that is an atrial pacing pulse.

Histogram bins may be assigned different atrial rate ranges in addition to or alternatively to separating sensed ventricular event counts based on atrial sensed and atrial paced cycles. In other examples, histogram bins may be assigned according to different patient activity levels (as determined from the accelerometer signal) for counting sensed far field ventricular events that occur during different levels of activity, e.g., during rest, activities of daily living, and high activity level greater than activities of daily living. Additionally or alternatively, histogram bins may be allocated for counting far field ventricular events that are sensed during different patient postures, e.g., side-lying posture vs. non-side lying postures, upright vs. non-upright, etc. These histogram bin counts of sensed far field ventricular events may be obtained by external device processor 22 at block 352 during an interrogation session with atrial pacemaker 14.

In other examples, histogram bin counts obtained by external device processor 52 from atrial pacemaker 14 at block 352 may include counts of other ventricular activity metrics such as counts of AV intervals corresponding to different bins of AV interval ranges, counts of integration metrics corresponding to different bins of integration metric ranges, etc. Multiple histogram bins may be designated in memory 210 for counting sensed far field ventricular events, integration metrics, and/or AV intervals according to atrial rate, atrial sensed or paced cycles, different patient physical activity levels, different patient postures, and/or according to different ranges of a given quantitative ventricular activity metric, such as AV intervals or integration metrics.

At block 354, external device processor 22 determines one or more AV synchrony metrics from the cardiac event data obtained at block 352. For example, external device processor 22 may determine each histogram bin count as a percentage of the total of all histogram bin counts, e.g., the total number of atrial cycles represented by the total combined histogram bin counts. In other examples, the AV synchrony metrics determined at block 354 may include a mean, median, range, variability or other statistical measure of centeredness and/or spread of the ventricular activity metrics determined.

Figure 9:
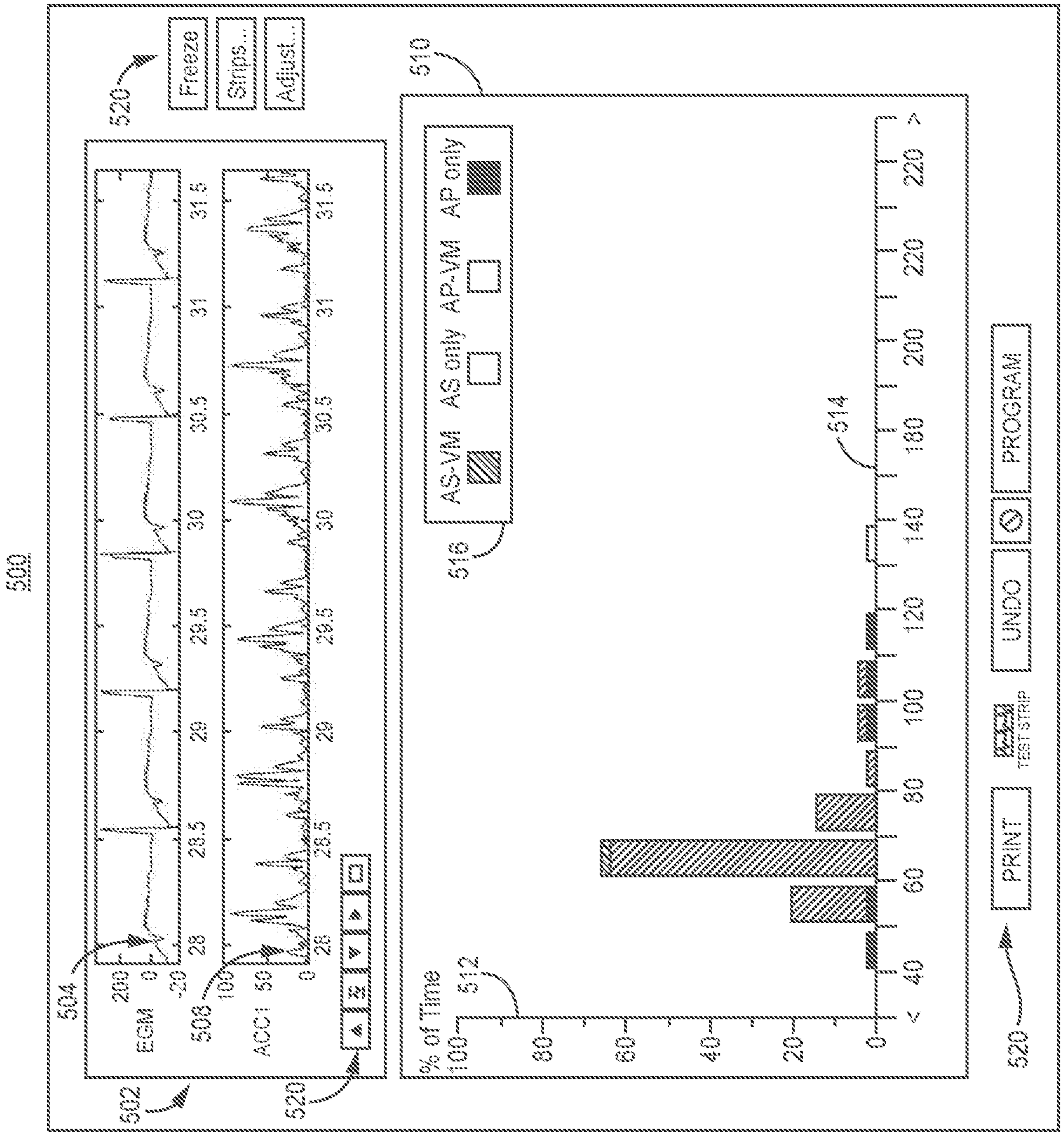
FIG. 9 is a diagram of a graphical user interface (GUI) that may be generated from data output by a medical device for display as a visual representation of AV synchrony data according to one example.

At block 356, external device processor 22 may generate output based on the determined AV synchrony metrics, and optionally related data and/or relevant cardiac signal episodes, for display by display unit 24. AV synchrony data may be displayed in a GUI to provide a visual representation of ventricular activity and corresponding AV synchrony. An example of a GUI representing AV synchrony data that may be displayed by external device 20 is shown in FIG. 9 and described below.

The use of the techniques disclosed herein may enable external device 20 to generate visualizations of cardiac signals, sensed cardiac events, determined ventricular activity metrics such as counts, integration metrics and AV interval data, and/or determined AV synchrony metrics. Such visualizations may enable an external device, such as external device 20, to inform a user as to how the RV pacemaker 12 is performing in sensing cardiac events and delivering atrial synchronized ventricular pacing pulses. In particular, the visual representations of ventricular activity metrics and AV synchrony metrics enable external device 20 to inform a user on the performance of RV pacemaker 12 in maintaining AV synchrony, using signals and data obtained by a different device, e.g., atrial pacemaker 14, independent of the sensing performance of the RV pacemaker 12 itself. The visual representation of the AV synchrony performance of RV pacemaker 12 may guide the clinician in selecting programmable sensing control parameter settings and/or pacing control parameter settings displayed by the GUI.

Adjustments to programmable control parameter settings may be made by a user interacting with user interface 26, which may be made via the GUI on display unit 24 and transmitted in a programming command. A user may reprogram a sensing and/or pacing control parameter setting used by atrial pacemaker 14 and/or by RV pacemaker 12 to improve the AV synchrony performance of RV pacemaker 12 by reducing cross-chamber oversensing and/or reducing over- or under-sensing of cardiac events by RV pacemaker 12.

Accordingly, the techniques set forth herein provide specific improvements to the computer-related field of programming medical devices that have practical applications. By providing the GUI or other user interface for displaying the data relating to AV synchrony performance of RV pacemaker 12, the likelihood of human error in identifying ventricular events that are properly synchronized with atrial events or asynchronous with atrial events and under what conditions ventricular asynchrony is most likely to occur is reduced. By presenting the AV synchrony metrics according to different conditions, such as during atrial pacing vs. atrial sensing, different heart rates, different patient physical activity, different patient body postures etc., the user may more readily troubleshoot the source of poor AV synchrony performance of RV pacemaker 12. Furthermore, the techniques disclosed herein may reduce the complexity of programming RV pacemaker 12 and/or atrial pacemaker 14 to improve AV synchrony performance of RV pacemaker 12. As such, the techniques disclosed herein may enable a medical device, such as RV pacemaker 12, to be programmed to reliably deliver atrial synchronized ventricular pacing in a manner that is simplified and patient-specific.

Figure 7:
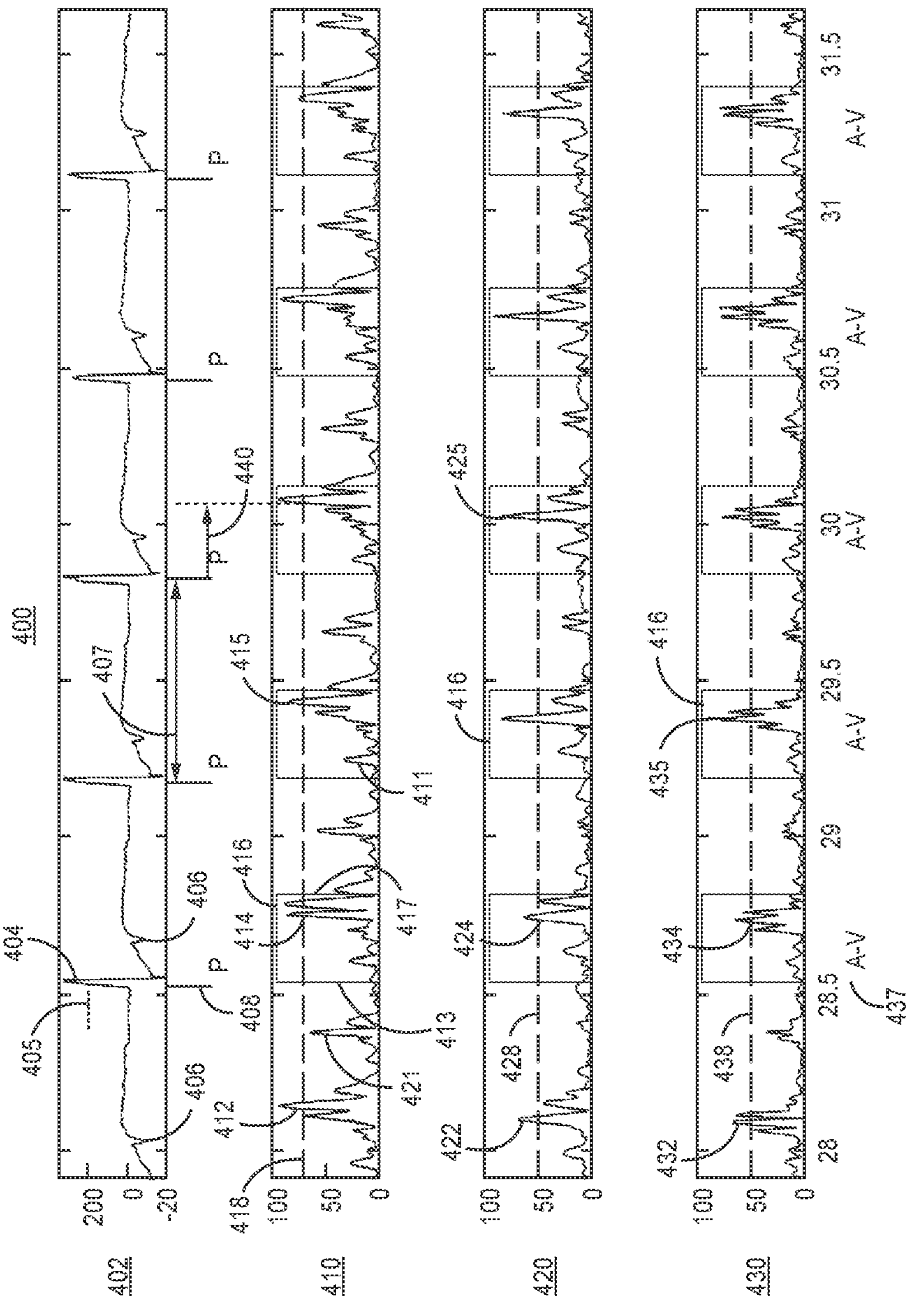
FIG. 7 is a diagram of an atrial electrical signal and simultaneously recorded accelerometer axis signals during AV synchrony.

FIG. 7 is a diagram 400 of an atrial electrical signal 402 and simultaneously recorded atrial accelerometer axis signals 410, 420 and 430 during AV synchrony. The atrial electrical signal 402 is an atrial EGM signal that may be produced by cardiac electrical sensing circuit 204 from signals sensed from the patient's heart via electrodes 162 and 164. The accelerometer axis signals 410, 420 and 430 are rectified filtered signals produced by mechanical signal sensing circuit 212. Each accelerometer axis signal 410, 420 and 430 may be produced from a respective axis of a three dimensional accelerometer included in mechanical signal sensing circuit 212. Each accelerometer axis signal 410, 420 and 430 is bandpass filtered, e.g., by a 10 to 30 Hz bandpass filter, and rectified by mechanical signal sensing circuit 212 and passed to control circuit 206.

Atrial electrical signal 402 includes atrial P-waves 404, each followed by an FFRW 406. Each axis signal 410, 420, and 430 includes far field ventricular event signals 412, 422 and 432, respectively, following each FFRW 406, representing ventricular myocardial contraction following ventricular myocardial depolarization. In the example of FIG. 7, AV synchrony is observed in that each atrial P-wave 404 is followed by an FFRW 406 and the subsequent mechanical contraction of the ventricles as evidenced by the ventricular systolic event signals 412, 422 and 432 of each accelerometer axis signal 410, 420 and 430 (respectively) following each P-wave 404. The term "ventricular systolic event signals" may generally refer to signals present in the accelerometer signal due to closure of the tricuspid and mitral valves, ventricular contraction, and/or opening of the pulmonary and aortic valves.

Each accelerometer axis signal 410, 420 and 430 may include a far field ventricular diastolic event signal 421 following the ventricular systolic event signal 412. The ventricular diastolic event signal 421 may correspond to the end of ventricular systole and start of ventricular diastole with the closure of the pulmonary and aortic valves and the ventricular relaxation and filling phase of the ventricular cycle. The techniques described herein for detecting a far field ventricular event may correspond to detecting the ventricular systolic event signals 412 (or 422 or 432) corresponding to ventricular contraction because the ventricular systolic event signal 412 is generally the largest amplitude signal in the accelerometer signal and therefore has the greatest signal strength promoting reliable determination of AV synchrony. It is recognized, however, that far field ventricular event signals of the accelerometer signal may include multiple signal peaks corresponding to mechanical activity of the ventricles during ventricular systole and/or diastole, such as the ventricular systolic event signal 412 and/or diastolic event signal 421, which may be detected by atrial pacemaker 14 when a ventricular pacing pulse is delivered by ventricular pacemaker 12 or when an intrinsic R-wave occurs. The absence of the ventricular event signals 412 and 421 during one or more atrial cycles and/or variability of the AV interval between an atrial P-wave (or atrial pacing pulse) and the subsequently sensed far field ventricular event may be evidence of AV asynchrony and poor AV synchrony pacing performance by RV pacemaker 12.

In some examples, both far field ventricular systolic event signals and far field ventricular diastolic event signals present in the accelerometer signal may contribute to a ventricular activity metric determined from the accelerometer signal, e.g., determined by integrating the accelerometer axis signal 410, 420 or 430, for determining AV synchrony metrics. Examples of ventricular activity metrics determined from the accelerometer signal that may include contributions of both ventricular systolic and ventricular diastolic event signals are described below, e.g., in conjunction with FIG. 10, where the ventricular activity metric is determined as an integration metric.

Each accelerometer axis signal may include an atrial event signal 411 corresponding to atrial contraction subsequent to each P-wave 404. In some examples, atrial cycles may be identified by identifying the atrial event signals 411 from the accelerometer signal. Since the atrial event signal 411 is relatively small in the accelerometer signals 410, 420 and 430 compared to the far field ventricular event signals, e.g., signals 412 and 421, the atrial P-wave 404 may be a more reliable signal for sensing atrial events and identifying atrial cycles and the atrial rate than the atrial event signal 411 of the accelerometer signal.

Cardiac electrical sensing circuit 204 generates a P-wave sensed event signal 408 in response to sensing each P-wave 404, e.g., in response to an atrial electrical signal crossing a P-wave sensing threshold 405. The P-wave sensing threshold 405 is shown relative to atrial EGM signal 452 in FIG. 7 for the sake of illustration. It is to be understood, however, that the P-wave sensed event signal 408 may be produced by event detector 224 in response to a P-wave sensing threshold crossing by a narrow-band filtered and rectified signal that is passed from rectifier and amplifier circuit 222 to event detector 224. Control circuit 206 may identify (and count) atrial cycles 407 by identifying an atrial electrical event in response to receiving each P-wave sensed event signal 408. In some examples, control circuit 206 is configured to identify an atrial cycle 407 in response to receiving a P-wave sensed event signal 408 and, in response to receiving the P-wave sensed event signal, set a ventricular event sensing window 416 applied to one, two or all three accelerometer axis signals 410, 420 and 430 (or a combined acceleration signal determined as a combination, e.g., a summation of two or all three accelerometer axis signals 410, 420 and 430). The ventricular event sensing window 416 may be set by control circuit 206 in response to each P-wave sensed event signal 408.

Ventricular event sensing window 416 may begin without a delay at starting time 413 upon receipt of P-wave sensed event signal 408. In other examples, sensing window 416 may have a starting time 413 that occurs at a predetermined delay after the P-wave sensed event signal 408, e.g., 50 ms, 100 ms, 150 ms or other interval, which may serve to blank any atrial acceleration signals, e.g., atrial event signal 411, present in the accelerometer axis signals 410, 420 and 430 immediately following the P-wave 404. While intrinsic P-waves 404 are shown to be sensed on each atrial cycle in the example diagram 400, it is to be understood that control circuit 206 may set a ventricular event sensing window 416 following any atrial electrical event, including sensed intrinsic P-waves and atrial pacing pulses, when monitoring for ventricular events for determining AV synchrony.

In the example shown, the ventricular event sensing window 416 has an ending time 417, which may be set to a predetermined time interval after the atrial electrical event, e.g., after P-wave sensed event signal 408 in this example. The ending time 417 may be set to 300 ms, 400 ms, 500 ms, 550 ms, 600 ms, 650 ms or other selected time interval after the atrial electrical event. In some examples, the ending time 417 is adjustable by control circuit 206 and may vary with the atrial rate, e.g., increase with longer atrial cycles and decrease with shorter atrial cycles, and/or set to a different time interval depending whether the atrial electrical event is paced or sensed. The sensing windows 416 are shown to have the same starting time 413 and ending time 417 for all three axis signals 410, 420 and 430. However, the sensing windows 416 may be set uniquely for each axis signal or combinations of signals when more than one axis signal and/or combinations of axis signals are being used for determining a ventricular activity metric. For example, the sensing window 416 may start earlier or later and/or end earlier or later for a particular axis signal due to the timing relative to the P-wave sensed event signal 408 of the maximum acceleration associated with ventricular contraction along the associated axis of the accelerometer 216.

Control circuit 206 may set a ventricular event sensing threshold 418, 428, or 438 applied to a selected one, two or all three of the accelerometer axis signals 410, 420, or 430, respectively. The ventricular event sensing threshold may be set during the sensing window 416. However, in some examples, the sensing window 416 is optional since ventricular event signals may be the largest signals in the acceleration signal. By setting the ventricular event sensing threshold to an appropriate level, e.g., greater than an atrial event signal amplitude, a ventricular event signal may be sensed whenever it may occur during an atrial cycle.

In some examples, any two or all three axis signals 410, 420 and 430 may be combined by control circuit 206, e.g., by summing time-aligned sample point amplitudes of the filtered and rectified axis signals. The various operations performed by control circuit 206 for sensing ventricular events for determining a ventricular activity metric as described herein, including setting a sensing window 416 (when used) and setting a ventricular event sensing threshold 418, 428 or 438, may be performed on the resulting signal determined as a combination of two or all three accelerometer axis signals 410, 420 and 430. The ventricular event sensing threshold, the selected axis signal (or combination of signals), and the ventricular event sensing window starting and ending times may be control parameters that may be programmable by a user using external device 20 or default values stored in memory 210.

In response to a ventricular event threshold crossing 414, 424, or 434 during the sensing window 416 by the respective accelerometer axis signal 410, 420 or 430, control circuit 206 senses the far field ventricular event and may determine the associated atrial cycle to be an AV synchrony cycle (labeled "A-V") 437. In some examples, the ventricular event sensing threshold 418, 428 or 438 may be set lower, even lower than the atrial event peak amplitude, and the number of sensing threshold crossings may be counted. When at least a threshold number of sensing threshold crossings is reached during the sensing window 416 or during an atrial cycle 407, the atrial cycle may be determined to be an AV synchrony cycle (A-V). The threshold number of sensing threshold crossings may be one, two, three, four or more and may include only positive-going crossings, only negative-going crossings or both positive and negative-going crossings.

Control circuit 206 may count an A-V cycle when at least one axis signal 410, 420 or 430 crosses the ventricular event threshold 418, 428 or 438 at least a threshold number of times during the sensing window 416. In other examples, control circuit 206 may require at least two or all three axis signals and/or one or more combination of two or all three axis signals to cross a respective ventricular event threshold in order to detect the associated atrial cycles as an A-V cycle. Control circuit 206 may count the number of atrial cycles that a far field ventricular event is not sensed within ventricular event sensing window 416 as AV asynchrony cycles. In some examples, control circuit 206 may count each AV synchrony cycle (A-V cycle) and each AV asynchrony cycle, or "A-only" cycle since no ventricular event is sensed, in a buffer (or histogram) in memory 210 to determine ventricular activity metrics as a counts of A-V cycles and/or counts of A-only cycles. Control circuit 206 or external device processor 22 may determine an AV synchrony metric as the percentage of A-V or A-only cycles out of the total number of counted atrial cycles. In the example of FIG. 400, the ventricular event sensing threshold 418, 428 and 438 is crossed during each ventricular event sensing window 416 resulting in 100% A-V cycles indicating AV synchrony is being maintained by RV pacemaker 12.

In the example of FIG. 7, the ventricular event sensing threshold 418 is set to 75 ADC units for axis signal 410, and the ventricular event sensing thresholds 428 and 438 are set to 50 ADC units for axis signals 420 and 430. One ADC unit may correspond to 11.8 milli-g (where 1 g is the acceleration of gravity) and 100 milli-g may correspond to 1 $m/s^2$ acceleration. Accordingly a threshold of 50 to 75 ADC units may correspond to an acceleration of approximately 6 $m/s^2$ to approximately 9 $m/s^2$. In other examples, the ventricular event threshold may be between 3 $m/s^2$ and 10 $m/s^2$. The ventricular event sensing threshold may be selected for a given axis signal or combination of axis signals and may be set differently for different single-axis signals and for different combinations of axis signals when more than one single-axis signal and/or combination of axis signals are being monitored for sensing ventricular events.

The ventricular event sensing threshold may be set and periodically updated based on a maximum peak amplitude 415, 425 or 435 of one or more ventricular event signals 412, 422 or 432 that are sensed from a respective axis signal 410, 420 or 430 when 100% AV synchrony is being detected by control circuit 206 (or confirmed by external device processor 22 by a user interacting with external device 20 of FIG. 1). When a combination of two or more axis signals 410, 420 and 430 is used for sensing far field ventricular events, the applied sensing threshold for sensing ventricular events from the combination signal may be based on a maximum peak amplitude of the acceleration signal determined from the combination signal during known AV synchrony.

In other examples, the threshold for detecting far field ventricular event signals may be set based on lower amplitude acceleration signals that are not intended to be sensed as ventricular events. Such lower amplitude signals may correspond to atrial contraction or other non-ventricular events, e.g., due to patient physical activity. The accelerometer signal may be filtered to attenuate the amplitude of lower amplitude signals that are not desired to be sensed. The amplitude of non-ventricular event signals may be determined and the threshold may be set greater than the amplitude of non-ventricular event signals (but less than an expected peak amplitude of ventricular event signals).

The ventricular event sensing threshold 418, 428, or 438 may be set to a percentage of or a difference less than a mean maximum peak amplitude, median maximum peak amplitude, greatest maximum peak amplitude, least maximum peak amplitude, or specified nth largest maximum peak amplitude that is determined by control circuit 206 over a specified number of atrial cycles when AV synchrony is determined. For example, control circuit 206 may set the ventricular event sensing threshold to 50%, 60%, 70% or other selected percentage of a minimum maximum peak amplitude 415 determined over 3, 6, 8, 10, 12 or other specified number of atrial cycles when AV synchrony is known to be present. Furthermore, the ventricular event sensing threshold applied to a selected accelerometer axis signal following sensed P-waves may be set uniquely from the ventricular event sensing threshold applied to the same accelerometer axis signal following delivered atrial pacing pulses.

Control circuit 206 may be configured to determine an AV interval 440 during one or more atrial cycles as a metric of ventricular activity. The term "AV interval" as used herein refers to the time from an atrial event, sensed or paced, to a sensed ventricular event or a selected feature or fiducial point of the far field ventricular event signal. The AV interval may be determined from an atrial event, electrical or mechanical (e.g., atrial event signal 421) to the next sensed ventricular event, which may be the systolic event signal (e.g., signal 412) or the diastolic event signal (e.g., signal 421) in the accelerometer signal. In the example of FIG. 7, control circuit 206 may determine the AV interval 440 as the time from the P-wave sensed event signal 408 (or a delivered atrial pacing pulse) to the ventricular event sensing threshold crossing 414, 424 or 434 by the respective far field ventricular systolic event signal 412, 422 or 432. AV intervals following atrial sensed events (A-sense AV intervals) may be determined and stored separately from AV intervals determined following atrial pacing pulses (A-pace AV intervals).

Control circuit 206 may buffer AV intervals in memory 210 for determining AV synchrony metrics. In some examples, AV intervals falling into two or more specified interval ranges may be counted in histogram bins allocated to the specified interval ranges. For example, one specified interval range may correspond to an expected AV delay used by RV pacemaker 12 when ventricular pacing pulses are correctly synchronized with atrial events and another specified interval range may correspond to relatively longer AV intervals indicative of AV asynchrony. A-sense AV intervals and A-pace AV intervals may be counted in separate histogram bins. Additionally or alternatively, histogram bins may be allocated according to atrial rate so that AV intervals falling into a specified interval range are counted in a specified atrial rate histogram bin corresponding to the rate of atrial events (or atrial cycle length), which may be further designated as an A-sense or A-pace histogram bin.

Control circuit 206 may compare a determined AV interval to an expected AV interval upper threshold or an expected AV interval range. The expected AV interval upper threshold or range may be programmable and may be based on a programmed AV delay used by RV pacemaker 12 for scheduling ventricular pacing pulses. When control circuit 206 determines that an AV interval is greater than the expected AV interval upper threshold, control circuit 206 may count an asynchronous cycle in the appropriate histogram bin (e.g., A-sense or A-pace histogram bin and/or according to atrial rate). When an AV interval is less than the expected AV interval upper threshold, control circuit 206 may count AV synchronous cycle in the appropriate histogram bin. In this way, the ventricular activity metrics may be determined by control circuit 206 as counts of AV intervals that correspond to AV synchrony or asynchrony. Control circuit 206 or external device processor 22 may determine AV synchrony metrics as the percentage of each histogram bin count out of the total AV intervals counted (or the total number of atrial cycles). When a far field ventricular event is not sensed during an atrial cycle, such that the AV interval cannot be determined by control circuit 206, the atrial cycle may be counted as an asynchronous cycle.

Figure 8:
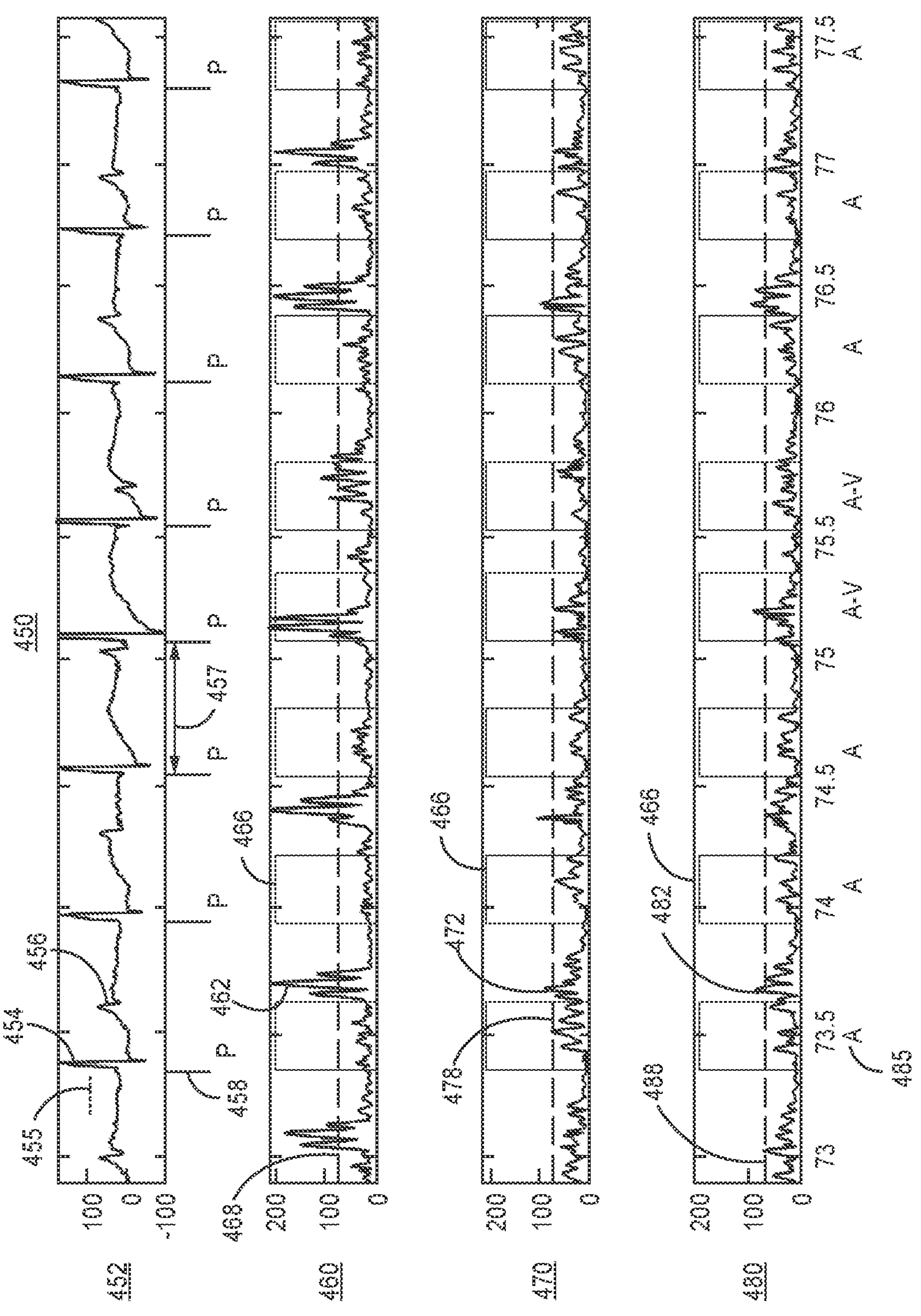
FIG. 8 is diagram of an atrial electrical signal and accelerometer axis signals that may be sensed by a medical device during AV asynchrony.

FIG. 8 is diagram 450 of an atrial electrical signal 452 and accelerometer axis signals 460, 470 and 480 that may be sensed by atrial pacemaker 14 during AV asynchrony. Atrial electrical signal 452 is an atrial EGM signal produced by cardiac electrical signal sensing circuit 204. Atrial electrical signal 452 includes atrial P-waves 454 and asynchronous FFRWs 456 occurring at varying times during each atrial cycle 457. Each accelerometer axis signal 460, 470 and 480 is a rectified bandpass filtered signal, which may be produced by accelerometer 216 from each signal generated by a respective axis of the three dimensional accelerometer. Each accelerometer signal 460, 470 and 480 includes a ventricular systolic event signal 462, 472 and 482, respectively, following an FFRW 456.

Cardiac electrical signal sensing circuit 204 generates a P-wave sensed event signal 458 in response to an atrial signal crossing a P-wave sensing threshold 455. The P-wave sensing threshold 455 is shown relative to atrial EGM signal 452 in FIG. 8 for the sake of illustration. It is to be understood that the P-wave sensed event signal 458 may be produced by event detector 224 in response to a P-wave sensing threshold crossing by a narrow-band filtered and rectified signal that is passed from rectifier and amplifier circuit 222 to event detector 224.

Control circuit 206 may optionally set a ventricular event sensing window 466 in response to each P-wave sensed event signal 458, as described above in conjunction with FIG. 7. Control circuit 206 may apply a ventricular event sensing threshold 468, 478 or 488 to the respective accelerometer axis signal 460, 470 or 480, which may be applied during the sensing window 466. As described above, a ventricular event sensing threshold may be applied to one, two or all three axis signals 460, 470 and 480 individually and/or to a combination of two and/or all three axis signals for detecting ventricular sensing threshold crossings. Control circuit 206 may count an atrial cycle as an AV synchrony cycle (labeled "A-V" in row 485) when the ventricular event sensing threshold is crossed during the sensing window 466 (or within a specified time interval from the atrial event). Control circuit 206 identifies an AV asynchrony cycle (labeled "A" in row 485) as any atrial cycle associated with only an atrial event and no ventricular event sensing threshold crossing during the sensing window 466.

As described above, an AV synchrony cycle may be counted by control circuit 206 when at least one axis signal 460, 470 or 480 crosses the respective sensing threshold 468, 478 or 488 during the ventricular event sensing window 466 or when one selected single axis or combination of axis signals crosses a respective ventricular event sensing threshold. In this example, an AV asynchrony cycle may be identified when none of the axis signals (or combination of axis signals) crosses the ventricular sensing threshold. In other examples, control circuit 206 may detect an AV synchrony cycle when at least two or all three axis signals cross a respective ventricular event sensing threshold or a combination signal composed of two or all three axis signals crosses a ventricular event sensing threshold. In this case, control circuit 206 may detect an AV asynchrony cycle as any atrial cycle during which a selected axis signal or selected combination of two or more axis signals does not cross the respective ventricular sensing threshold. Control circuit 206 may determine a ventricular activity metric as a count of sensed far field ventricular events over the identified atrial cycles so that the AV synchrony metric may be determined as a percentage of AV synchrony cycles out of the identified atrial cycles.

In FIG. 8, a majority of atrial cycles are AV asynchronous cycles, in which an atrial event is not followed by a ventricular event within the ventricular event sensing window 466. When a threshold percentage of atrial cycles are AV asynchronous cycles (or conversely when less than a threshold percentage of atrial cycles are AV synchronous cycles), control circuit 206 may determine AV asynchrony as an indication of poor AV synchrony pacing performance by RV pacemaker 12. In response to determining poor AV synchrony, control circuit 206 may transmit an AV asynchrony notification signal. The AV asynchrony notification signal may be received by RV pacemaker 12, which may cause RV pacemaker 12 to adjust a sensing and/or pacing control parameter. Additionally or alternatively, the AV asynchrony notification signal may be transmitted to external device 20 to notify a clinician.

In the examples of FIGS. 7 and 8, the accelerometer signal feature used to sense a far field ventricular event is based on the amplitude of the accelerometer signal and in particular the amplitude of the accelerometer signal being greater than a ventricular event sensing threshold amplitude during a ventricular event sensing window following each atrial electrical event. In other examples, control circuit 206 may determine one or more features of a selected accelerometer signal during the sensing windows 416 and 466 for determining if a far field ventricular event is sensed during the sensing window as evidence of AV synchrony. For example, control circuit 206 may determine the maximum signal amplitude during the sensing window, the number of peaks, the signal width, the signal area, the maximum slope or other signal features or combinations of features. One or more features may be used to sense or detect a far field ventricular event during the sensing window 416 or 466 for counting an AV synchrony cycle. Control circuit 206 may determine one or more of these signal features to determine if the far field ventricular event signal is sensed for determining a count of AV synchrony cycles as the ventricular activity metric at block 304 of FIG. 5.

FIG. 9 is a diagram of a GUI 500 that may be generated from data output by control circuit 206 and stored in memory 210. Ventricular activity metrics determined as sensed ventricular event counts may be stored in memory 210 and transmitted to external device processor 22 for display by display unit 24 as a visual representation of AV synchrony data according to some examples. Display unit 24 of external device 20 may be a touch-sensitive screen that is configured to both display GUI 500 to a user as well as provide touch-sensitive regions of GUI 500 that allow the user to provide input to GUI 500. In other examples, a user may navigate to different user input portions 520 of GUI 500, e.g., selectable windows, pop-up-windows, menus, icons, buttons or the like, using a mouse, keyboard or other user interface input device. Various user input portions 520 of GUI 500 may be included to enable to a user to advance, reverse, zoom in and out, print, freeze, or save data displayed in GUI 500 or to select a programming window for programming atrial pacemaker 14, as examples.

GUI 500 may include a cardiac signal window 502 and a data window 510. In cardiac electrical signal window 502, a cardiac electrical signal (EGM) 504 and/or an acceleration signal (ACC1) 508 may be displayed. The cardiac signal(s) displayed in cardiac signal window 502 may be real time signals transmitted from atrial pacemaker 14. In some instances, the cardiac signal(s) displayed in cardiac signal window 502 may be a signal episode stored by atrial pacemaker 14 in memory 210 corresponding to a determination of an AV synchrony metric, e.g., an episode when asynchrony is determined. The asynchrony may be determined by control circuit 206 when the percentage of atrial cycles that include a synchronized ventricular event is less than a threshold percentage, e.g., less than 90%, less than 80%, less than 70%, less than 60% or less than 50% as examples. A cardiac signal episode representative of a time period of asynchrony may be displayed to provide the user information for determining a cause of the asynchrony, enabling corrective action to be taken, e.g., adjusting programmable atrial sensing control parameters in the RV pacemaker 12, adjusting ventricular pacing control parameters in the RV pacemaker 12, adjusting atrial pacing control parameters in atrial pacemaker 14 and/or adjusting atrial sensing control parameters for sensing both atrial and ventricular events in atrial pacemaker 14 and/or control parameters for determining ventricular activity metrics, AV synchrony metrics, and/or determining AV asynchrony.

Data window 510 may include a table, graph, or other visual representation of the AV synchrony metrics determined by control circuit 206 or external device processor 22 based on histogram counts or other data received from atrial pacemaker 14. In the example shown, the histogram bin counts accumulated by control circuit 206 in memory 210 are graphed as a percentage of time (e.g., percentage of all atrial cycles since implant or since the last time AV synchrony data was received from atrial pacemaker 14). The histogram bin counts determined as ventricular activity metrics may be transmitted to external device 20, stored in external device memory 23 and used by external device processor 22 to output percentages of the total number of atrial cycles for generating the bar graph in data window 510.

As described above, control circuit 206 may sense far field ventricular event signals from a cardiac signal sensed from an atrial location to identify atrial cycles that include a far field ventricular event signal. For each atrial event, sensed or paced, control circuit 206 may increment the count of a histogram bin in memory 210 that corresponds to the type of atrial event, sensed or paced, the atrial rate, and whether a ventricular event was sensed or not. In this example, a histogram bin is allocated to count atrial cycles in atrial rate ranges (bins) between 40 to 140 beats per minute in increments of 10 beats per minute (bin width). For each atrial rate range, a histogram bin is allocated to store a count of atrial sensed events that are not followed by a sensed ventricular event before the next atrial event (labeled "AS only" in legend 516), atrial sensed events that are followed by a ventricular mechanical event sensed from the accelerometer signal before the next atrial event (labeled "AS-VM" in legend 516), atrial paced events not followed by a sensed ventricular event ("AP only"), and atrial paced events followed by a sensed ventricular mechanical event ("AP-VM"). Atrial rate is plotted along the x-axis 514 and the percentage of time (percentage of all atrial cycles) is plotted along the y-axis 512.

The legend 516 distinguishes the histogram counts plotted in the bar graph shown in data window 510 for each type of atrial cycle (AS-VM, AS only, AP-VM, or AP only) for each atrial rate range. The atrial rate may be determined for each atrial cycle counted based on the time interval between a leading atrial event (sensed or paced) and the next atrial event. The atrial rate for paced atrial events will correspond to the current atrial pacing interval, which may be a programmed lower rate interval or a temporary rate response pacing interval. The atrial rate for sensed atrial events will correspond to the time expired on a pacing escape interval at the time a P-wave sensed event signal is received by control circuit 206 from sensing circuit 204.

In various examples, data window 510 may include a graphical and/or tabular representation of total AV synchronous atrial cycles and total AV asynchronous atrial cycles counted (for all atrial rates combined), a breakdown of AV asynchronous atrial paced cycles counted and AV synchronous atrial paced cycles (for all atrial rates combined), a breakdown of the total AV asynchronous atrial sensed cycles and AV synchronous paced cycles for all atrial rates combined, or other distributions of the histogram counts stored by atrial pacemaker 14.

The AV synchrony data represented in data window 510 is one example of a visual representation of ventricular activity metrics and AV synchrony metrics that may be determined and displayed according to the techniques disclosed herein. As described above, a graph or table of data relating to ventricular activity metrics determined as sensed ventricular event counts, AV intervals and/or integration metrics, as examples, may be generated for display including ventricular activity metrics determined during different patient physical activity level and/or different patient postures in addition to or instead of the different atrial rates and different atrial paced or sensed atrial rhythms as shown in FIG. 9.

Figure 10:
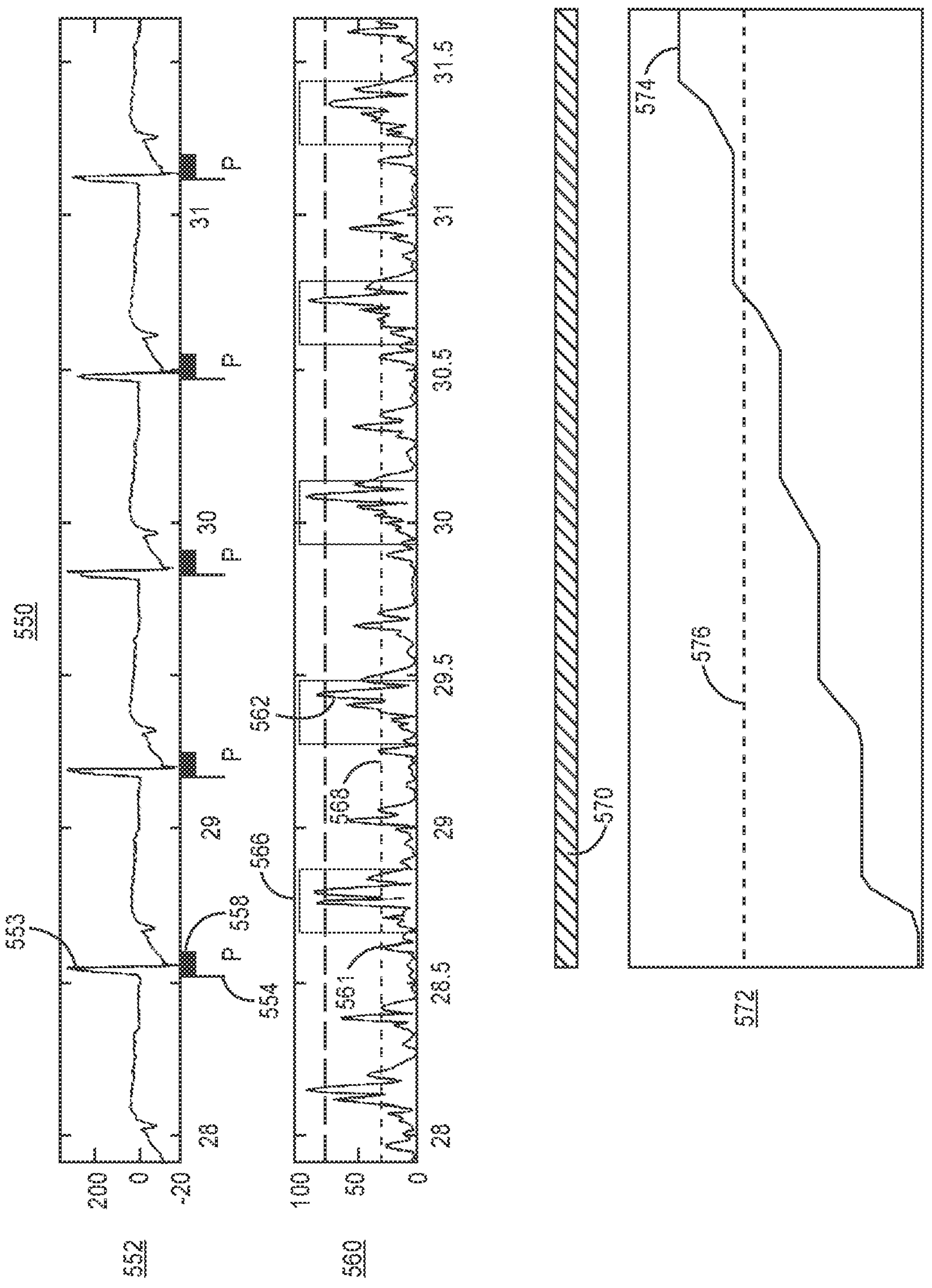
FIG. 10 is a diagram of a cardiac electrical signal, a corresponding acceleration signal, and an integration metric determined as a ventricular activity metric from the acceleration signal according to one example.

FIG. 10 is a diagram 550 of a cardiac electrical signal 552, a corresponding acceleration signal 560, and an integration metric 572 determined as a ventricular activity metric from the acceleration signal 560 according to one example. The cardiac electrical signal 552 is an atrial EGM signal that may be produced by sensing circuit 204 from signals sensed from the patient's heart via electrodes 162 and 164 and passed to control circuit 206. Cardiac electrical signal 552 includes atrial P-waves 553 corresponding to P-wave sensed event signals 556 generated by cardiac electrical signal sensing circuit 204. The acceleration signal 560 is a rectified, filtered signal produced by mechanical signal sensing circuit 212. For example, acceleration signal 560 may be bandpass filtered, e.g., by a 10 to 30 Hz bandpass filter, and rectified by mechanical signal sensing circuit 212 and passed to control circuit 206. The acceleration signal 560 in this example is a single axis acceleration signal but may alternatively be a combination (e.g., a summation) of two axis signals or all three axis signals of a three axis accelerometer 216 in other examples. In some implementations, control circuit 206 may receive two or all three single axis acceleration signals from accelerometer 216 and determine one or more combinations of two or all three axis signals. Acceleration signal 560 includes atrial event signals 561 and ventricular event signals 562 as generally described above.

Integration metric 572 is a ventricular activity metric determined from the acceleration signal 560 for assessing AV synchrony. Integration metric 572 is determined by summing the amplitudes of sample points of acceleration signal 560 over a specified integration time interval 570. Integration metric 572 is therefore correlated to the ventricular activity, e.g., the ventricular rate, during the integration time interval since the final value 574 reached at the end of the integration time interval 570 is correlated to the number of ventricular event signals 562 (and area of each ventricular event signal) contributing to the integration metric.

The integration time interval 570 may encompass multiple atrial cycles as shown in FIG. 10 so that the final value 574 is an indication of the likelihood of whether or not a ventricular event occurred during each atrial cycle. The integration metric final value 574 may be compared to an AV synchrony threshold 576. When the integration metric is greater than the threshold value 576, AV synchrony may be determined by control circuit 206. When the integration metric final value 574 does not reach the threshold value 576, control circuit 206 may determine AV asynchrony for the time period represented by the integration time interval 570.

The integration time interval 570 may be started in response to a P-wave sensed event signal 554 or an atrial pacing pulse and ended after a specified number of atrial cycles. Alternatively, the integration time interval 570 may be started independent of atrial event timing and extend a predetermined time period. The number of atrial events or cycles or the atrial rate may be determined during the integration time interval 570 so that the final value 574 of the integration metric can be normalized by the number of atrial events or the atrial rate. The normalized integration metric may be determined by control circuit 206 as an AV synchrony metric. When the normalized integration metric is greater than a threshold value, AV synchrony is determined. When the normalized integration metric is less than a threshold value, AV asynchrony is determined. When the integration time interval 570 is controlled as a fixed number of atrial cycles, the final value 574 may be compared directly to a predetermined threshold for determining AV synchrony or asynchrony without normalizing by the atrial rate.

In some examples, control circuit 206 optionally starts a post-atrial blanking period 558 in response to each P-wave sensed event signal 554 and each atrial pacing pulse. The post-atrial blanking period 558 may be applied to acceleration signal 560 during integration time interval 570 to blank the atrial event signal 561 from contributing to the final value 574 of the integration metric 572. The integration metric 572 may be determined by control circuit 206 by summing the acceleration signal sample point amplitudes outside of post atrial blanking periods 558 during integration time interval 570. Atrial blanking period 558 may be 100 to 200 ms long or between 120 to 150 ms long, as examples. In this way, the final value 574 of integration metric 572 may be highly correlated to ventricular activity during the integration time interval 570 instead of a combination of atrial and ventricular activity.

In other examples, control circuit 206 may set ventricular event sensing windows 566 in response to each P-wave sensed event signal 554 (and each atrial pacing pulse). The integration metric 572 may be determined by summing the sample point amplitudes of acceleration signal 560 only during each of the ventricular event sensing windows 566 that occur during the integration time interval 570. In this way, the final value 574 of the integration metric reached at the expiration of the integration time interval 570 is highly correlated to ventricular activity that occurs at an expected AV interval during each atrial cycle within the integration time interval 570 instead of including ventricular activity that occurs at any time during the atrial cycle and atrial activity in the integration metric. In this way, the integration metric 572 is highly correlated to atrial synchronized ventricular activity that occurs during the integration time interval 570.

Additionally or alternatively, control circuit 206 may set an amplitude threshold 568. Control circuit 206 may sum all acceleration signal sample point amplitudes that are greater than amplitude threshold 568 during the integration time interval 570. Post-atrial blanking periods 558 may or may not be applied when amplitude threshold 568 is applied since the amplitude threshold 568 may eliminate the lower amplitude atrial events 561 (and any baseline noise) from contributing to the integration metric 572. The use of atrial blanking periods 558, amplitude threshold 568 and/or ventricular event sensing windows 566 is optional, however. In some examples, all sample points during the integration time interval 570 may be summed to obtain the integration metric 572, without applying any blanking periods 558, ventricular event sensing windows 566 or amplitude threshold 568. The final value 574 of the integration metric may be normalized by the number of atrial cycles or the atrial rate so that the resulting AV synchrony metric is representative of the relationship between ventricular activity and atrial activity during the integration time interval 570. The normalized integration metric is therefore representative of the degree of AV synchrony. A relatively low normalized integration metric represents AV asynchrony and a relatively higher normalized integration metric represents AV synchrony.

The integration metric 572 may be used by control circuit 206 to classify each integration time interval 570 as either AV synchrony or AV asynchrony. Control circuit 206 may accumulate counts of AV synchrony time intervals and AV asynchrony time intervals. The counts of AV synchrony and AV asynchrony time intervals may be stored in histogram bins in memory 210. As described above, histogram bins may be separately allocated for counting AV synchrony time intervals and AV asynchrony time intervals according to atrial rhythm (sensed or paced), atrial rate, patient physical activity, and/or patient posture.

Instead of determining each integration metric 572 over multiple atrial cycles as shown in the example of FIG. 10, the integration metric may be determined over a single atrial cycle in some examples. When determined over a single atrial cycle, the final value of the integration metric may be compared to a threshold value for indicating whether a ventricular event is present during the atrial cycle or not. The integration time interval applied over a single atrial cycle may be applied only during a ventricular event sensing window 566 in some examples so that the final value of the integration metric is an indication of whether or not a ventricular event occurs within an expected AV interval during one atrial cycle.

In this way, a ventricular activity metric may be determined beat-by-beat by integrating the accelerometer signal 560 over the ventricular event sensing window 566 or over each atrial cycle (and optionally outside post-atrial blanking period 558 in some examples) for counting AV synchrony cycles and AV asynchrony cycles. The ventricular activity metric determined as an integration metric over an individual atrial cycle may be compared to a threshold by control circuit 206 for classifying each atrial cycle as an AV synchrony cycle or an AV asynchrony cycle. For example, control circuit 206 may sum the rectified sample point amplitudes of the acceleration signal 560 over sensing window 566. In some cases, control circuit 206 may sum only sample point amplitudes exceeding a specified minimum threshold amplitude 568. The summation of the sample point amplitudes may be compared to a threshold value for discriminating between AV synchrony and AV asynchrony for the given atrial cycle. When the summed amplitudes are less than the threshold value, a histogram count corresponding to AV asynchrony may be increased. When the summed amplitudes are greater than the threshold value, control circuit 206 may increase a histogram count corresponding to AV synchrony.

In other examples, instead of summing the acceleration signal amplitude points to determine the integration metric, control circuit 206 may determine a count of acceleration signal sample points that exceed a specified minimum threshold amplitude 568 in the rectified acceleration signal 560 during ventricular sensing window 566 (or during the entire integration time interval 506 outside optional atrial blanking periods 558) and compare the count to a threshold count for discriminating between AV synchrony and AV asynchrony atrial cycles. When the sample point count is greater than the threshold, control circuit 206 may count an AV synchrony cycle. When the sample point count is less than the threshold, control circuit 206 may count an AV asynchrony cycle.

Figure 11:
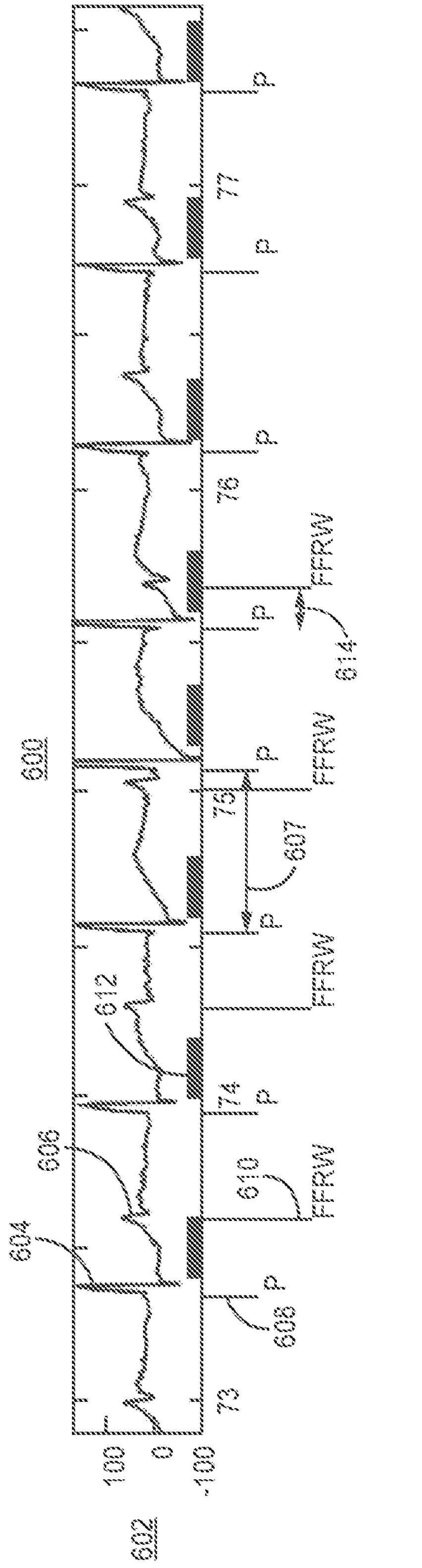
FIG. 11 is a diagram of an atrial electrical signal illustrating techniques for determining an AV synchrony metric based on sensing far-field R-waves (FFRWs) from the atrial signal.

FIG. 11 is a diagram 600 of an atrial electrical signal 602 illustrating techniques for determining an AV synchrony metric based on sensing FFRWs. Atrial electrical signal 602 is shown as a wideband filtered EGM signal including P-waves 604 and FFRWs 606. Sensing circuit 204 or control circuit 206 of atrial pacemaker 14 may be configured to sense FFRWs 606 from a sensed atrial electrical signal 602 (e.g., from wideband filtered signal 602 or from a narrowband filtered and rectified atrial signal) for use in determining an AV synchrony metric in some examples. Sensing circuit 204 may include an FFRW sensing channel for sensing FFRWs 606. Sensing circuit 204 may apply a post-atrial blanking period (e.g., as shown in FIG. 10) and/or an FFRW sensing window 612 applied to the atrial electrical signal. The FFRW 606 may be sensed by sensing circuit 204 from the sensed atrial electrical signal during the FFRW sensing window 612 in response to a threshold amplitude crossing or threshold slew rate for instance. Sensing circuit 204 may pass an FFRW sensed event signal 610 to control circuit 206.

Control circuit 206 may increment a histogram counter in memory 210 each time an FFRW sensed event signal 610 is received within an expected maximum AV interval, e.g., within FFRW sensing window 612, after a P-wave sensed event signal or atrial pacing pulse. The histogram counters may be allocated for separately counting FFRWs sensed following sensed P-waves and FFRWs sensed following atrial pacing pulses. The histogram counters may be allocated to multiple atrial rate ranges, patient physical activity levels, and/or patient postures as described above.

In other examples, the wideband filtered atrial EGM signal 602 may be passed to control circuit 206 from sensing circuit 204. Control circuit 206 may detect FFRWs 606 based on a morphology analysis of EGM signal 602. Control circuit 206 may analyze the EGM signal 602 after a post-atrial blanking period and/or within an FFRW sensing window 612 (which may be set to encompass an expected AV interval). Control circuit 206 may determine one or more features of the EGM signal, e.g., a peak-to-peak amplitude, polarity, signal area, signal width, or overall waveform morphology using a wavelet transform or other morphology analysis techniques. Control circuit 206 may compare one or more determined morphology features to criteria for sensing the FFRW 606. In response to FFRW sensing criteria being met within an expected maximum AV interval from an atrial event, control circuit 206 may increment an AV synchrony histogram counter. When the FFRW criteria are not met before the next atrial event, sensed or paced, control circuit 206 may increment an AV asynchrony (atrial event only) histogram counter.

Additionally or alternatively, control circuit 206 may determine the AV interval 614 from an atrial electrical event, e.g., a P-wave sensed event signal 608 or an atrial pacing pulse, to the FFRW sensed event signal 610 or a specified feature or fiducial point of the FFRW signal 606. The AV interval 614 may be determined for each sensed FFRW and stored in memory 210. Control circuit 206 may be configured to determine a variability (or measure of spread) of AV intervals as an AV synchrony metric for a given number of atrial cycles, e.g., 2, 3, 5, 10, 20, 30, or more cycles. When the variability is greater than a threshold variability, control circuit 206 may determine AV asynchrony. When control circuit 206 is configured to determine AV intervals, the FFRW sensing window 612 is optional. Control circuit 206 may determine the AV intervals from the atrial electrical event to an FFRW sensed at any time during an atrial cycle 607 as the ventricular activity metrics then determine the variability, range, summation of successive absolute differences or other variability measure of the AV intervals as an AV synchrony metric.

Control circuit 206 may count AV intervals according to different AV interval ranges in designated histogram bins in memory 210 in some examples. External device 20 may generate a display of the histogram of AV intervals. The range between the highest and lowest occupied histogram bins may be compared to a threshold range and/or the histogram bin having the highest frequency of AV intervals may be compared to a threshold AV interval (or range) for assessing AV synchrony. For example, control circuit 206 may determine AV asynchrony in response to the range of AV intervals exceeding a variability limit and/or the mean, median or mode being greater than a threshold AV interval.

Figure 12:
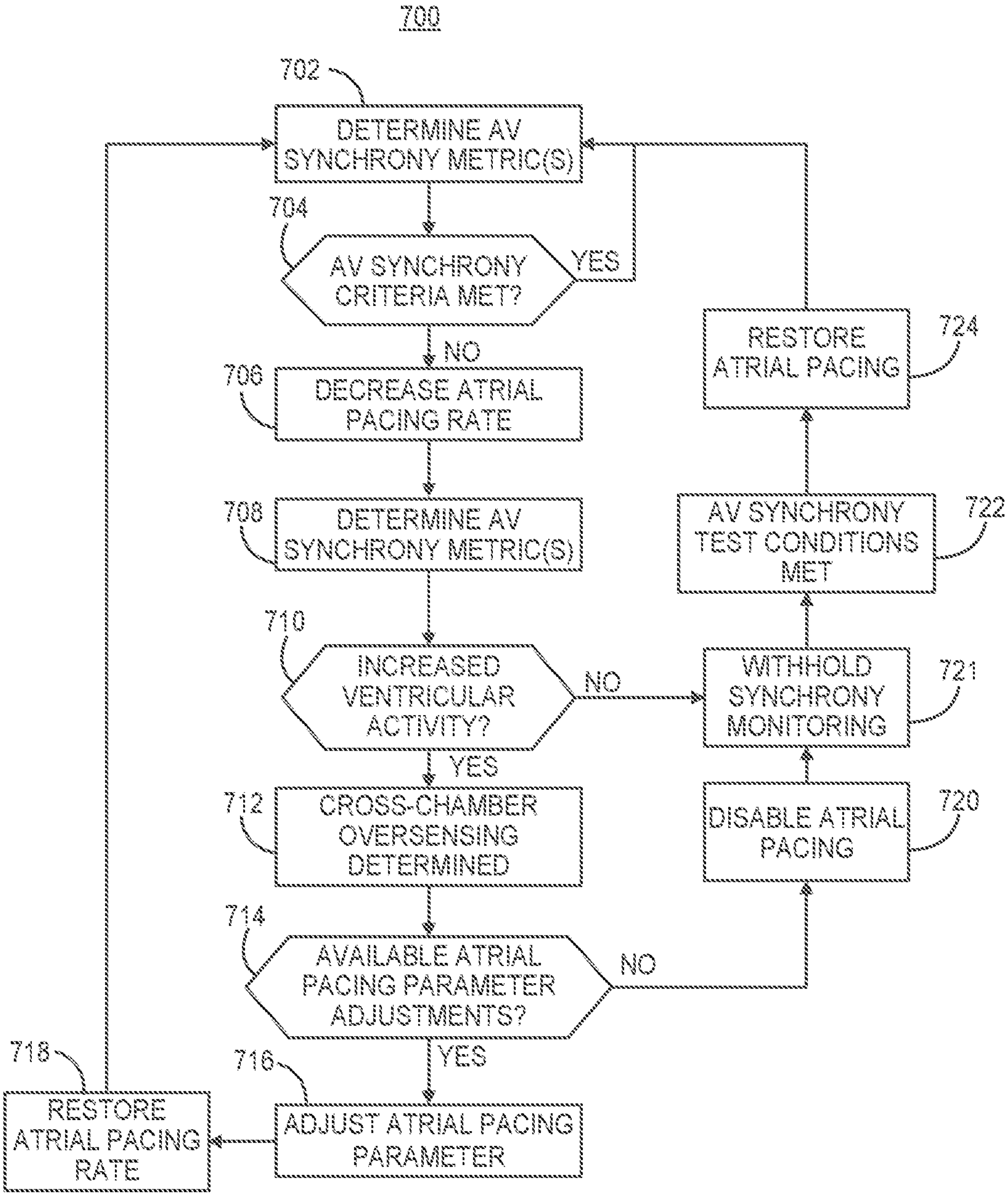
FIG. 12 is a flow chart of a method that may be performed by an atrial pacemaker for assessing and responding to AV synchrony performance of a ventricular pacemaker.

FIG. 12 is a flow chart 700 of a method that may be performed by an atrial pacemaker 14 for assessing and responding to AV synchrony performance of a ventricular pacemaker. At block 702, control circuit 206 of atrial pacemaker 14 determines an AV synchrony metric according to any of the examples given above. Control circuit 206 may determine the AV synchrony metric by determining one or more of a ratio of sensed ventricular event rate to a rate of atrial events, a count or percentage of atrial cycles including a ventricular event, an integration metric correlated to ventricular rate, or an AV interval mean, median, mode, variability or range, as examples.

In some examples, control circuit 206 may determine more than one AV synchrony metric. For example, one AV synchrony metric may be determined from the accelerometer signal or the atrial electrical signal (e.g., FFRW sensing) during ventricular event sensing windows so that the AV synchrony metric is correlated to ventricular activity within an expected AV time interval, indicating atrial synchronized ventricular activity. A second AV synchrony metric may be determined from the accelerometer signal or the atrial electrical signal during the atrial cycles that includes any ventricular activity occurring outside the ventricular event sensing windows. The second AV synchrony metric may be determined using the accelerometer signal sensed over the entire atrial cycle, only outside a post-atrial blanking interval, or only outside the ventricular event sensing window. When determined over the entire atrial cycle or only outside the post-atrial blanking period, the second AV synchrony metric includes ventricular activity that occurs at any time during the atrial cycle and therefore is correlated to both atrial synchronous and asynchronous ventricular activity. When determined over the atrial cycle outside the ventricular event sensing window, the AV synchrony metric includes ventricular activity that is asynchronous to atrial activity and may exclude synchronous ventricular activity and is therefore inversely correlated to synchronous ventricular activity and correlated to asynchronous ventricular activity.

At block 704, control circuit 206 may compare the determined AV synchrony metric(s) to criteria for determining acceptable AV synchrony. The AV synchrony criteria applied at block 704 may require a 1:1 ratio of ventricular rate to atrial rate or a threshold percentage of atrial cycles including a sensed ventricular event, which may be required to be within an expected AV interval (e.g., sensed within a ventricular event sensing window). The AV synchrony criteria may require an integration metric be equal to or greater than a threshold value or within an AV synchrony range. The integration metric may be normalized by an atrial event count so that the integration metric is correlated to the ratio of ventricular activity to atrial activity. The AV synchrony criteria may require an average of AV intervals or other metric of AV interval centeredness be less than an expected AV interval maximum threshold or within a threshold range. Additionally or alternatively, the AV synchrony criteria may require that the AV interval variability or range be less than a threshold variability or within a threshold range. One or a combination of AV synchrony metrics may be required to meet respective criteria for AV synchrony criteria to be met at block 704 and may include any of the example AV synchrony criteria described herein.

When AV synchrony criteria are met at block 704, control circuit 206 returns to block 702 to continue determining the AV synchrony metric(s). The AV synchrony metrics may be determined on a scheduled or ongoing basis, and the determination of whether AV synchrony criteria are met may be performed each time an AV synchrony metric is updated or less frequently. For example, the AV synchrony criteria may be applied once a day, once per hour or at other scheduled time intervals to AV synchrony data stored in memory 210. To illustrate, histogram counters may be updated on a beat-by-beat basis. Histogram counters may be allocated for storing counts of AV synchrony atrial cycles and AV asynchrony cycles over a preceding time interval, e.g., the most recent n cycles, one minute, one hour, 24 hours or other specified time interval. The histogram bin counts may be compared to AV synchrony criteria at the end of each specified time interval. In some examples, memory 210 may include histogram bins allocated for storing AV synchrony and AV asynchrony atrial cycle counts since the time of atrial pacemaker implant or since a most recent interrogation session in addition to histogram bins allocated for storing counts associated with shorter time intervals.

In response to AV synchrony criteria not being met, control circuit 206 may perform a cross-chamber oversensing test beginning at block 706. When AV asynchrony is determined, one cause of the AV asynchrony may be oversensing of atrial pacing pulses delivered by atrial pacemaker 14 as R-waves by the RV pacemaker 12. Cross-chamber oversensing of atrial pacing pulses as false R-waves may cause ventricular pacing pulses to be withheld by the RV pacemaker 12, resulting in AV synchrony criteria not being met. RV pacemaker 12 may be configured to sense atrial events from an accelerometer signal sensed from within the ventricle. If atrial pacing pulses delivered by atrial pacemaker 14 are falsely sensed as R-waves by RV pacemaker 12, the subsequent atrial mechanical event following the atrial pacing pulse may occur during a post-ventricular blanking or refractory period, before an atrial event sensing window, and therefore may not be sensed for tracking ventricular pacing pulses to the atrial rate.

Atrial pacemaker 14 may perform a cross-chamber oversensing test by decreasing the atrial pacing rate, e.g., by extending the atrial pacing interval, at block 706 and determining if increased ventricular activity is detected at block 710. The increased ventricular activity may be detected based on determining one or more AV synchrony metric(s) during a slower atrial pacing rate at block 708. When the atrial pacing interval is increased, a ventricular pacing interval is more likely to expire before the next atrial pacing pulse so that a ventricular pacing pulse is delivered by RV pacemaker 12 before an atrial pacing pulse can be oversensed causing the ventricular pacing pulse to be inhibited. In some examples, the atrial pacing interval is increased at block 706 so that the corresponding atrial pacing rate is slower than the programmed ventricular lower pacing rate. For example, a user may program the cross-chamber oversensing test atrial pacing rate to be less than the programmed ventricular lower pacing rate. In other examples, atrial pacing rate is decreased at block 706 by withholding atrial pacing for one or more cardiac cycles.

If oversensed atrial pacing pulses were previously causing inhibition of ventricular pacing, RV pacemaker 12 may begin pacing at the ventricular lower pacing rate, asynchronously with the atrial rate when the atrial pacing rate is less than the programmed ventricular lower pacing rate. In some instances, some atrial pacing pulses at the reduced atrial pacing rate may still be oversensed such that the ventricular pacing rate is not necessarily equal to the ventricular lower rate on all paced cycles since some ventricular pacing pulses may still be inhibited. An overall increase in the number of delivered ventricular pacing pulses (and decrease in the number of inhibited ventricular pacing pulses), however, is expected.

After adjusting the atrial pacing rate, atrial pacemaker control circuit 206 may determine one or more AV synchrony metrics at block 708, which may be the same or different than the AV synchrony metric(s) determined at block 702. In various examples, control circuit 206 may count the atrial cycles that include a ventricular event sensed at any time in the atrial cycle, determine AV interval variability, and/or determine an integration metric of the acceleration signal. During the cross-chamber oversensing test, the AV synchrony metric(s) may be determined at block 708 over the same or a shorter time period or number of cardiac cycles as the AV synchrony metric(s) determined at block 702. At block 710, control circuit 206 determines if the AV synchrony metric determined from a sensed cardiac signal during the reduced atrial pacing rate meets increased ventricular activity criteria at block 710.

For example, an integration metric that is determined over at least one atrial cycle, including ventricular activity outside a ventricular event sensing window, is expected to increase after reducing the atrial pacing rate if cross-chamber oversensing was contributing to the AV asynchrony determined at block 704. In another example, a histogram count of sensed ventricular events, which may be counted within and/or outside a ventricular event sensing window, is expected to increase after decreasing the atrial pacing rate if cross-chamber oversensing was causing ventricular pacing inhibition before decreasing the atrial pacing rate. Other AV synchrony metrics described herein or other ventricular activity metrics may be determined for detecting increased ventricular activity at block 710 that represents an increase in the frequency of ventricular events after decreasing the atrial pacing rate compare to before decreasing the atrial pacing rate.

When control circuit 206 determines that increased ventricular activity criteria are met at block 710 after decreasing the atrial pacing rate, control circuit 206 determines at block 712 that cross-chamber oversensing of atrial pacing pulses by the RV pacemaker 12 is a likely cause of the AV asynchrony detected at block 704. Adjustments to the atrial pacing control parameters may reduce the likelihood and frequency of cross-chamber oversensing to either restore AV synchrony or at least avoid withholding ventricular pacing, even if it may be asynchronous.

At block 714, control circuit 206 may determine if alternative atrial pacing pulse settings are available. Control circuit 206 may adjust an atrial pacing pulse setting at block 716 to reduce the likelihood of cross-chamber oversensing by RV pacemaker 12. For instance, the atrial pacing pulse width may be reduced to a lower setting. A shorter pacing pulse width may be less likely to be oversensed by the RV pacemaker 12. When the pacing pulse width is shortened, the pacing pulse amplitude may be increased according to a capture threshold test to avoid loss of capture of the atria. Control circuit 206 may execute a pacing capture threshold test at multiple pulse widths to establish a strength-duration curve and store the corresponding pacing capture threshold amplitude for each respective pulse width in memory 210. In this way, when the pacing pulse width is reduced, control circuit 206 may adjust the pacing pulse amplitude to a higher amplitude as needed to maintain atrial capture, according to the strength-duration data stored in memory 210.

After adjusting the pacing pulse parameter(s) at block 716, control circuit 206 may increase or restore the atrial pacing rate at block 718 and return to block 702 to reassess AV synchrony during the increased or restored atrial pacing rate using the adjusted pacing pulse width and/or amplitude. Control circuit 206 may make multiple attempts at adjusting the atrial pacing pulse parameters (e.g., multiple combinations of pulse width and pulse amplitude) to reduce the likelihood of cross-chamber oversensing by RV pacemaker 12. For example, after a first adjustment at block 716, control circuit 206 may decrease the atrial pacing pulse width again at block 716 when cross-chamber oversensing is determined again at block 712, until all available lower pacing pulse width settings (or a predetermined maximum number of attempts) have been exhausted. Different combinations of pulse width and pulse amplitude based on the strength-duration curve determined for the patient (or based on capture tests as the pacing pulse width and amplitude are adjusted) may be tested until AV synchrony is determined at block 704 or all available combinations of pulse width and amplitude have been attempted.

In some instances, a change in the atrial pacing rate may allow the RV pacemaker 12 to regain reliable atrial event sensing and restore AV synchrony. As such, the atrial pacing parameters that may be adjusted at block 716 may include pulse width, pulse amplitude, and/or pacing rate. Any atrial pacing parameter adjustments that result in restoring AV synchrony may be stored in memory 210 for transmission to external device 20 for display to a user. AV synchrony monitoring data transmitted to external device 20 may include cardiac signal episodes representative of the AV asynchrony detected and/or AV synchrony after being restored.

If all available atrial pacing pulse parameter settings (or a maximum number of attempts) have been tested ("no" branch of block 714) without determining AV synchrony at block 704, control circuit 206 may disable atrial pacing at block 720. The patient may benefit from pacing the ventricle at a regular rate even though ventricular pacing may be asynchronous with the atrial rate. In this way, withholding of ventricular pacing pulses due to cross-chamber oversensing of atrial pacing pulses by RV pacemaker 12 is avoided, reducing the likelihood of ventricular asystole, a ventricular escape rhythm or irregular ventricular paced rate.

When control circuit 206 determines that the increased ventricular activity criteria are not met at block 710 during a slower atrial pacing rate, cross-chamber oversensing of atrial pacing pulses is not indicated. Other factors may be causing the AV asynchrony determined at block 704, e.g., oversensing of noise, undersensing of atrial events, or other factors. When atrial pacing is disabled at block 720 and/or when cross-chamber oversensing is not determined ("no" branch of block 710), atrial pacemaker 14 may withhold AV synchrony monitoring at block 721 for a predetermined time interval or until other AV synchrony test conditions are met at block 722.

Control circuit 206 may wait a specified time period, which may be programmable, before returning to block 702 to determine the AV synchrony metric(s) again. The specified time period may be several minutes, one hour, several hours, or one day as examples. In other examples, control circuit 206 may detect one or more conditions for restarting AV synchrony monitoring, in addition to or alternatively to waiting a specified time period. Such conditions may include, but are not limited to, a change in pacing electrode impedance, a change in patient posture (determined from the accelerometer signal), a change in the intrinsic atrial rate, a change in the far field ventricular event rate, a change in patient physical activity, or other condition that may result in a change in the sensing and pacing performance of RV pacemaker 12. If atrial pacing has been previously disabled at block 720, control circuit 206 may restore atrial pacing at block 724 before returning to block 702 to resume determining AV synchrony metric(s). Atrial pacing parameters may be restored to the most recent parameter settings or the last known atrial pacing pulse parameters that did not result in a cross-chamber oversensing determination.

While not shown explicitly in FIG. 12, it is to be understood that atrial pacemaker 14 may transmit an AV asynchrony notification at block 704 when AV synchrony criteria are not met and/or at block 710 in response to not determining an increase in ventricular activity during a reduced atrial pacing rate. As described above, a transmitted AV asynchrony notification received by RV pacemaker 12 may enable RV pacemaker 12 to perform one or more adjustments to ventricular sensing control parameters, atrial sensing control parameters and/or ventricular pacing parameters in an attempt to restore AV synchrony. Furthermore, a transmitted AV asynchrony notification may be received by external device 20 for notifying a clinician or caregiver or the patient that AV asynchrony is determined, which may warrant medical attention.

In some examples, an AV asynchrony notification is transmitted at block 710 in response to determining that ventricular activity is not increased after decreasing the atrial pacing rate. The AV asynchrony notification may be transmitted at block 721 instead of withholding AV synchrony monitoring in some examples. In this way, atrial pacemaker 14 may continue monitoring for AV synchrony so that a return of AV synchrony due to any adjustments that may be made by the RV pacemaker 12 is detected at block 704. Additionally or alternatively, the AV asynchrony notification may be transmitted at block 714 after atrial pacing parameter adjustments for reducing the likelihood of cross-chamber oversensing are exhausted. When AV synchrony cannot be restored by adjusting atrial pacing parameters, the RV pacemaker 12 may respond to the AV asynchrony notification by adjusting pacing parameters in an attempt to restore AV synchrony or at least promote ventricular pacing support at a lower rate.

It should be understood that, depending on the example, certain acts or events of any of the methods described herein can be performed in a different sequence, may be added, merged, or left out altogether (e.g., not all described acts or events are necessary for the practice of the method). Moreover, in certain examples, acts or events may be performed concurrently, e.g., through multi-threaded processing, interrupt processing, or multiple processors, rather than sequentially. In addition, while certain aspects of this disclosure are described as being performed by a single circuit or unit for purposes of clarity, it should be understood that the techniques of this disclosure may be performed by a combination of units or circuits associated with, for example, a medical device.

In one or more examples, the functions described may be implemented in hardware, software, firmware, or any combination thereof. If implemented in software, the functions may be stored as one or more instructions or code on a computer-readable medium and executed by a hardware-based processing unit. Computer-readable media may include computer-readable storage media, which corresponds to a tangible medium such as data storage media (e.g., RAM, ROM, EEPROM, flash memory, or any other medium that can be used to store desired program code in the form of instructions or data structures and that can be accessed by a computer).

Instructions may be executed by one or more processors, such as one or more digital signal processors (DSPs), general purpose microprocessors, application specific integrated circuits (ASICs), field programmable logic arrays (FPLAs), or other equivalent integrated or discrete logic circuitry. Accordingly, the term "processor," as used herein may refer to any of the foregoing structure or any other structure suitable for implementation of the techniques described herein. Also, the techniques could be fully implemented in one or more circuits or logic elements.

Thus, a medical device has been presented in the foregoing description with reference to specific examples. It is to be understood that various aspects disclosed herein may be combined in different combinations than the specific combinations presented in the accompanying drawings. It is appreciated that various modifications to the referenced examples may be made without departing from the scope of the disclosure and the following claims.

What is claimed is:

1. A medical device system comprising:

sensing circuitry configured to:

- sense one or more cardiac signals; and
- sense atrial event signals from the one or more cardiac signals;

pulse generating circuitry configured to deliver atrial pacing pulses based on the sensed atrial event signals; and control circuitry configured to:

- control the pulse generating circuitry to deliver the atrial pacing pulses based on the sensed atrial event signals;

determine a ventricular activity metric from the one or more cardiac signals;

based on the ventricular activity metric, determine an atrioventricular synchrony metric that represents the performance of a ventricular pacemaker in maintaining synchrony between ventricular pacing pulses delivered by the ventricular pacemaker and at least one of the sensed atrial event signals or the delivered atrial pacing pulses;

detect atrioventricular asynchrony based on the atrioventricular synchrony metric;

generate an output based on the atrioventricular synchrony metric by at least adjusting an atrial pacing control parameter in response to detecting the atrioventricular asynchrony; and control the pulse generating circuitry according to the adjusted atrial pacing control parameter; and a memory configured to store data corresponding to the atrioventricular synchrony metric in response to the output generated by the control circuit.

2. The medical device system of claim 1, wherein the control circuitry is further configured to:

identify ventricular event signals from the one or more cardiac signals; and identify atrial cycles based on the sensed atrial events and the delivered atrial pacing pulses; and determine the ventricular activity metric by determining a count of the atrial cycles that include a ventricular event signal.

3. The medical device system of claim 1, wherein the control circuitry is further configured to determine the ventricular activity metric by determining an integration metric of a cardiac signal of the one or more cardiac signals sensed over an integration time interval.

4. The medical device of claim 1 wherein the control circuitry is further configured to determine the ventricular activity metric by determining a plurality of atrioventricular time intervals from the one or more cardiac signals.

5. The medical device system of claim 1 wherein the control circuitry is further configured to adjust the atrial pacing control parameter by one of decreasing an atrial pacing rate or disabling atrial pacing pulse delivery by the pulse generating circuitry.

6. The medical device system of claim 1 further comprising:

an atrial pacemaker comprising:

a housing that encloses the sensing circuitry, the pulse generating circuitry and the control circuitry; and a first telemetry circuit configured to transmit data corresponding to the atrioventricular synchrony metric stored in the memory; and an external device comprising:

a second telemetry circuit configured to receive the transmitted data; and a display unit configured to generate a display of at least a portion of the transmitted data in a user interface.

7. The medical device system of claim 6 wherein the control circuitry is further configured to:

identify ventricular event signals from an atrial signal of the one or more cardiac signals, the atrial signal sensed from an atrium of the heart;

determine the ventricular activity metric by determining a count of atrial cycles comprising a ventricular event signal present in the atrial signal;

store the count of atrial cycles comprising a ventricular event signal in the memory; and control the first telemetry circuit to transmit the data comprising the count of atrial cycles comprising a ventricular event signal.

8. The medical device system of claim 7 wherein:

the control circuitry is further configured to:

determine a first percentage of the count of atrial cycles comprising a ventricular event signal that include a sensed atrial event followed by the ventricular event signals; and determine a second percentage of the count of atrial cycles comprising a ventricular event signal that include an atrial pacing pulse followed by the ventricular event signal; and the display unit is further configured to display at least one of the first percentage or the second percentage.

9. The medical device system of claim 1 further comprising:

a first telemetry circuit configured to transmit data corresponding to the atrioventricular synchrony metric stored in the memory; and the ventricular pacemaker configured to:

receive the transmitted data; and adjust at least one of a sensing control parameter or a ventricular pacing control parameter in response to receiving the transmitted data.

10. The medical device of claim 1 wherein the control circuitry is further configured to adjust the atrial pacing control parameter by adjusting a timing of the atrial pacing pulses delivered by the pulse generating circuitry.

11. A method, comprising:

sensing one or more cardiac signals;

sensing atrial event signals from the one or more cardiac signals;

generating atrial pacing pulses based on the sensed atrial event signals;

determining a ventricular activity metric from the one or more cardiac signals;

based on the ventricular activity metric, determining an atrioventricular synchrony metric that represents the performance of a ventricular pacemaker in maintaining synchrony between ventricular pacing pulses delivered by the ventricular pacemaker and at least one of the sensed atrial event signals or the delivered atrial pacing pulses; and detecting atrioventricular asynchrony based on the atrioventricular synchrony metric;

generating an output based on the atrioventricular synchrony metric;

adjusting, by an implantable medical device, at least one of a sensing control parameter or a pacing control parameter in response to the generated output by adjusting at least an atrial pacing control parameter in response to detecting the atrioventricular asynchrony; and storing data corresponding to the atrioventricular synchrony metric in response to the generated output.

12. The method of claim 11, further comprising:

identifying ventricular event signals from the one or more cardiac signals; and identifying atrial cycles based on the sensed atrial events and the delivered atrial pacing pulses; and determining the ventricular activity metric by determining a count of the atrial cycles that include a ventricular event signal.

13. The method of claim 11, wherein determining the ventricular activity metric comprises determining an integration metric of a cardiac signal of the one or more cardiac signals sensed over an integration time interval.

14. The method of claim 11 further comprising determining the ventricular activity metric by determining a plurality of atrioventricular time intervals from the one or more cardiac signals.

15. The method of claim 11 further comprising adjusting the atrial pacing control parameter by one of decreasing an atrial pacing rate or disabling the atrial pacing.

16. The method of claim 11 further comprising:

transmitting the stored data corresponding to the atrioventricular synchrony metric; and displaying at least a portion of the transmitted stored data in a user interface.

17. The method of claim 16 further comprising:

identifying ventricular event signals from an atrial signal of the one or more cardiac signals, the atrial signal sensed from an atrium of the heart;

determining the ventricular activity metric by determining a count of atrial cycles comprising a ventricular event signal present in the atrial signal;

storing the count of atrial cycles comprising a ventricular event signal; and transmitting the stored data comprising the count of atrial cycles comprising a ventricular event signal.

18. The method of claim 17 further comprising:

determining a first percentage of the count of atrial cycles comprising a ventricular event signal that include a sensed atrial event followed by the ventricular event signal;

determining a second percentage of the count of atrial cycles comprising a ventricular event signal that include an atrial pacing pulse followed by the ventricular event signal; and displaying at least one of the first percentage or the second percentage.

19. The method of claim 11 further comprising:

transmitting the stored data corresponding to the atrioventricular synchrony metric by a first communication circuit; and receiving the transmitted stored data by a second communication circuit; and adjusting, in response to receiving the transmitted stored data, at least one of a sensing control parameter or a ventricular pacing control parameter in response to receiving the transmitted data.

20. The method of claim 11 further comprising adjusting the atrial pacing control parameter by adjusting a timing of the atrial pacing pulses.

21. A non-transitory, computer-readable storage medium comprising a set of instructions which, when executed by processing circuitry of a medical device system, cause the medical device system to:

sense one or more cardiac signals;

sense atrial event signals from the one or more cardiac signals;

deliver atrial pacing pulses based on the sensed atrial event signals;

determine a ventricular activity metric from the received ventricular event signals;

based on the ventricular activity metric, determine an atrioventricular synchrony metric that represents the performance of a ventricular pacemaker in maintaining synchrony between ventricular pacing pulses delivered by the ventricular pacemaker and at least one of the sensed atrial event signals or the delivered atrial pacing pulses;

detect atrioventricular asynchrony based on the atrioventricular synchrony metric;

generate an output based on the atrioventricular synchrony metric by at least adjusting an atrial pacing control parameter in response to detecting the atrioventricular asynchrony;

control delivery of the atrial pacing pulses according to the adjusted atrial pacing control parameter;

transmit, by an implantable communication circuit of the medical device system, data corresponding to the atrioventricular synchrony metric in response to the generated output;

receive, by an external communication circuit of the medical device system, the transmitted data corresponding to the atrioventricular synchrony metric; and display the data corresponding to the atrioventricular synchrony metric in a user interface.

* * * * *